(12) United States Patent  
Schmitz

(10) Patent No.: US 7,780,156 B2  
(45) Date of Patent: Aug. 24, 2010

(54) WEB HANDLING PROCESS AND EQUIPMENT

(76) Inventor: Christoph Schmitz, Dr. Lieser Str. 2, Euskirchen Stotzheim (DE) 53881

( * ) Notice: Subject to any disclaimer, the term of this patent is extended or adjusted under 35 U.S.C. 154(b) by 397 days.

(21) Appl. No.: 11/908,493

(22) PCT Filed: Mar. 29, 2005

(86) PCT No.: PCT/IB2005/000845

§ 371 (c)(1), (2), (4) Date: Sep. 12, 2007

(87) PCT Pub. No.: WO2006/103487

PCT Pub. Date: Oct. 5, 2006

(65) Prior Publication Data

US 2008/0197164 A1    Aug. 21, 2008

(51) Int. Cl.  
*B65H 37/04* (2006.01)
(52) U.S. Cl. .................. 270/52.07; 270/52.08
(58) Field of Classification Search ........... 270/5.01, 270/5.02, 5.03, 16, 40, 41, 52.07, 52.08, 270/52.09; 493/358, 359, 422, 441  
See application file for complete search history.

(56) References Cited

U.S. PATENT DOCUMENTS

| | | | |
|---|---|---|---|
| 3,526,563 A | 9/1970 | Schott, Jr. | |
| 3,850,425 A * | 11/1974 | Marcalus et al. | 270/40 |
| 5,016,801 A | 5/1991 | Gilat et al. | |
| 5,693,165 A | 12/1997 | Schmitz et al. | |
| 6,283,905 B1 * | 9/2001 | Singh | 493/360 |
| 6,394,730 B1 * | 5/2002 | Manico et al. | 412/9 |
| 7,037,251 B2 * | 5/2006 | Stefanoni | 493/359 |
| 7,384,386 B2 * | 6/2008 | Sosalla | 493/441 |
| 2007/0129230 A1 * | 6/2007 | Sosalla | 493/441 |

FOREIGN PATENT DOCUMENTS

| DE | 2447656 A1 | 9/1975 |
|---|---|---|
| EP | 915049 A | 5/1999 |
| EP | 974323 A | 1/2000 |

* cited by examiner

*Primary Examiner*—Gene Crawford  
*Assistant Examiner*—Leslie A Nicholson, III  
(74) *Attorney, Agent, or Firm*—David A. Guerra

(57) ABSTRACT

The present invention relates to a method and equipment for the handling of web materials (200), such as essentially continuous webs of plastic films, textiles, non-wovens, or paper, or the like, or of parts or pieces of such webs. In particular execution, it relates to modifying the movement of such web materials (200), so as to allow other process steps to be performed on or with these web materials more easily. Particular aspects relate to the creation of a cross-directional fold in the web material and the combining of web materials (200) with other materials.

14 Claims, 17 Drawing Sheets

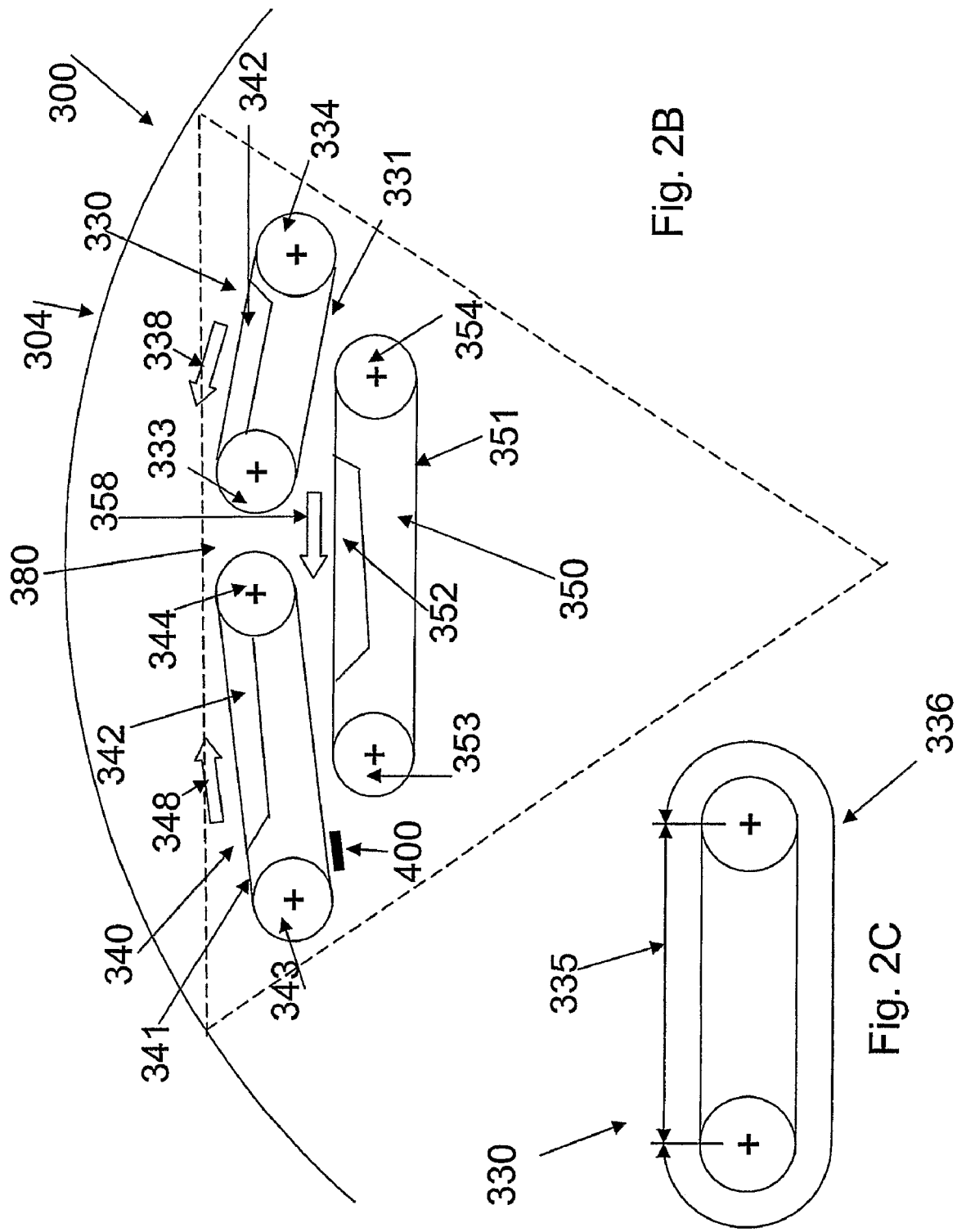

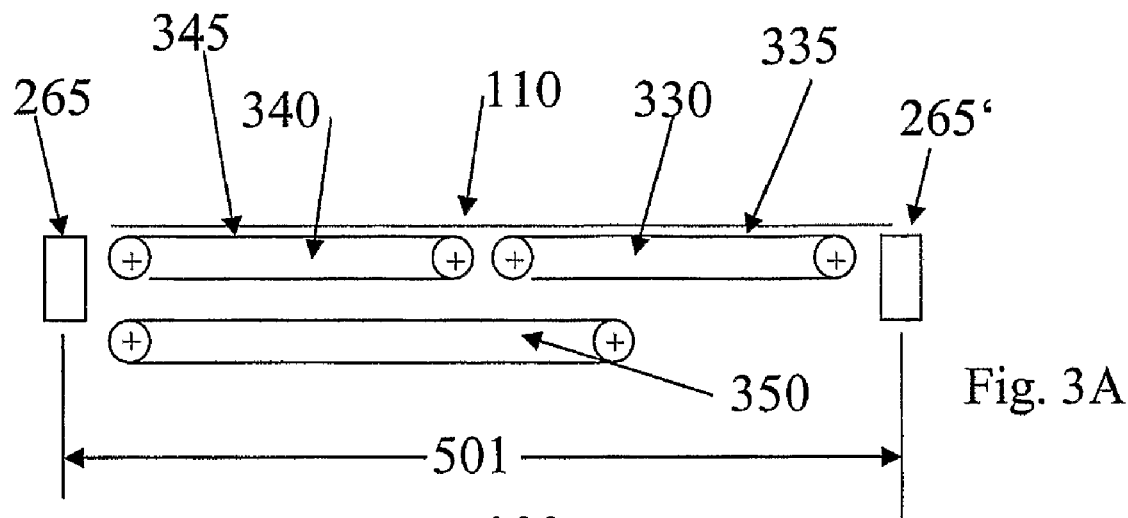
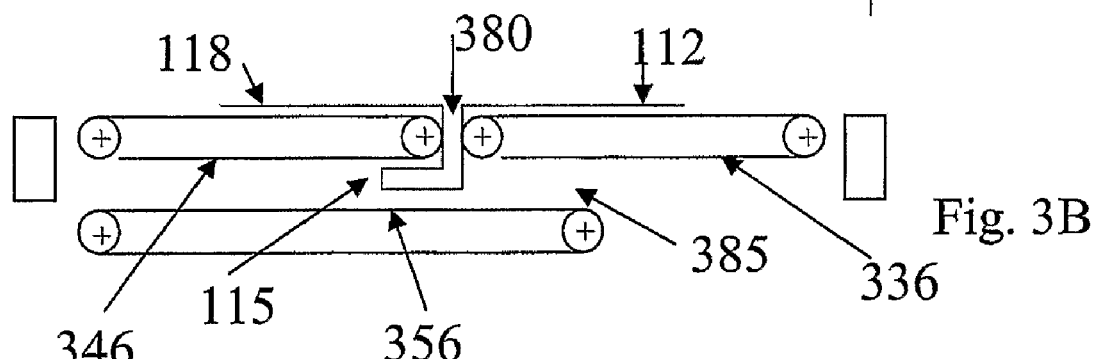
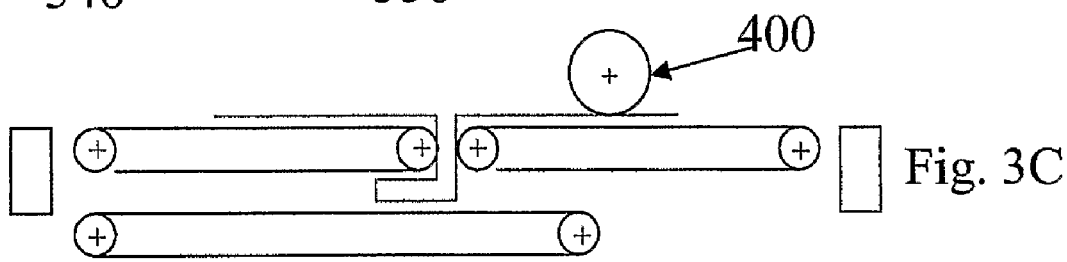
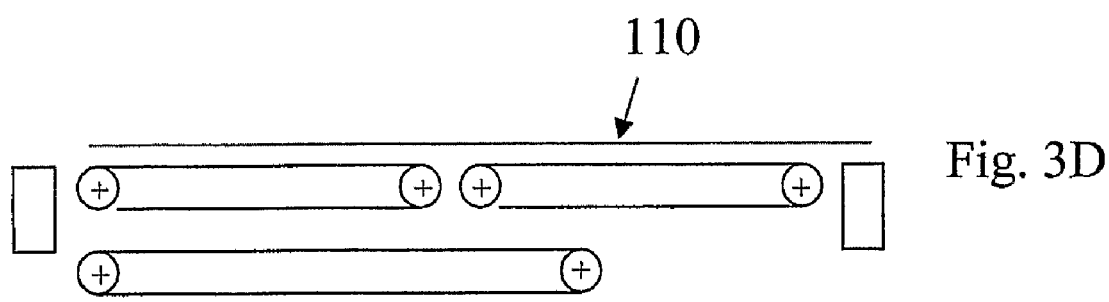
Fig. 3

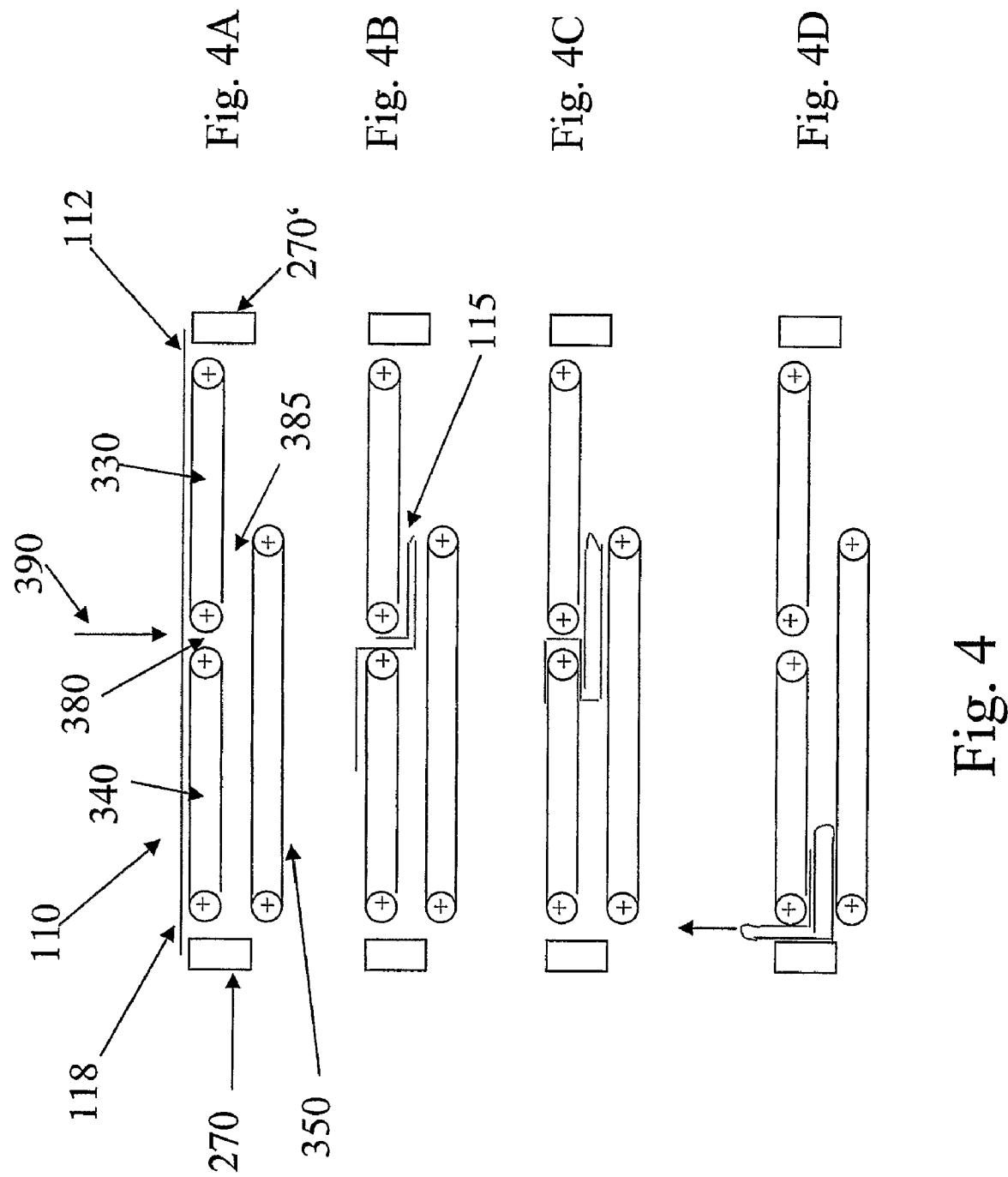

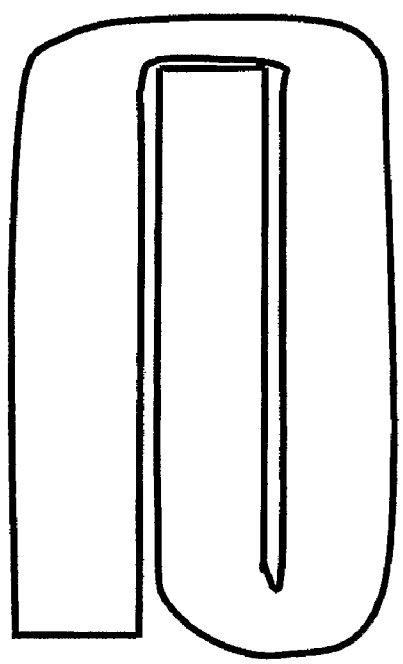
Fig. 5A
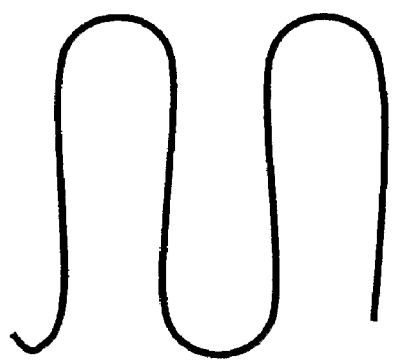
Fig. 5C
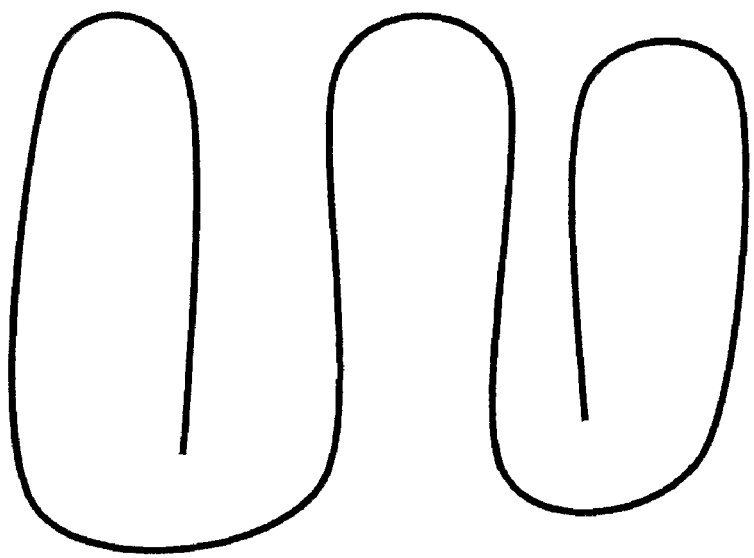
Fig. 5B
Fig. 5D
Fig. 5

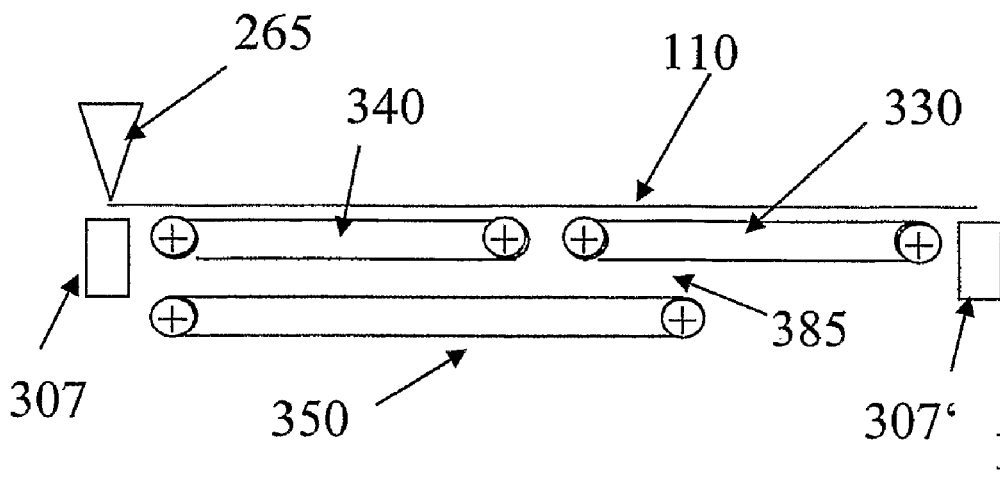
Fig. 7A
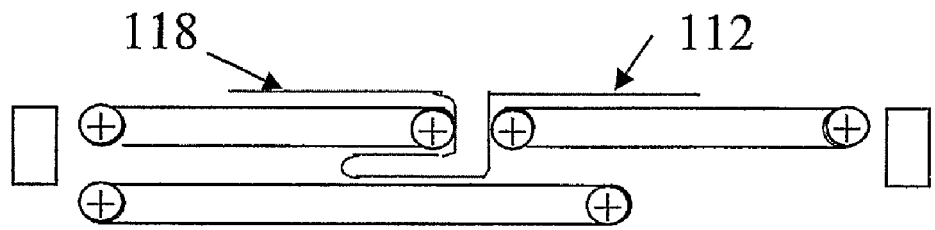
Fig. 7B
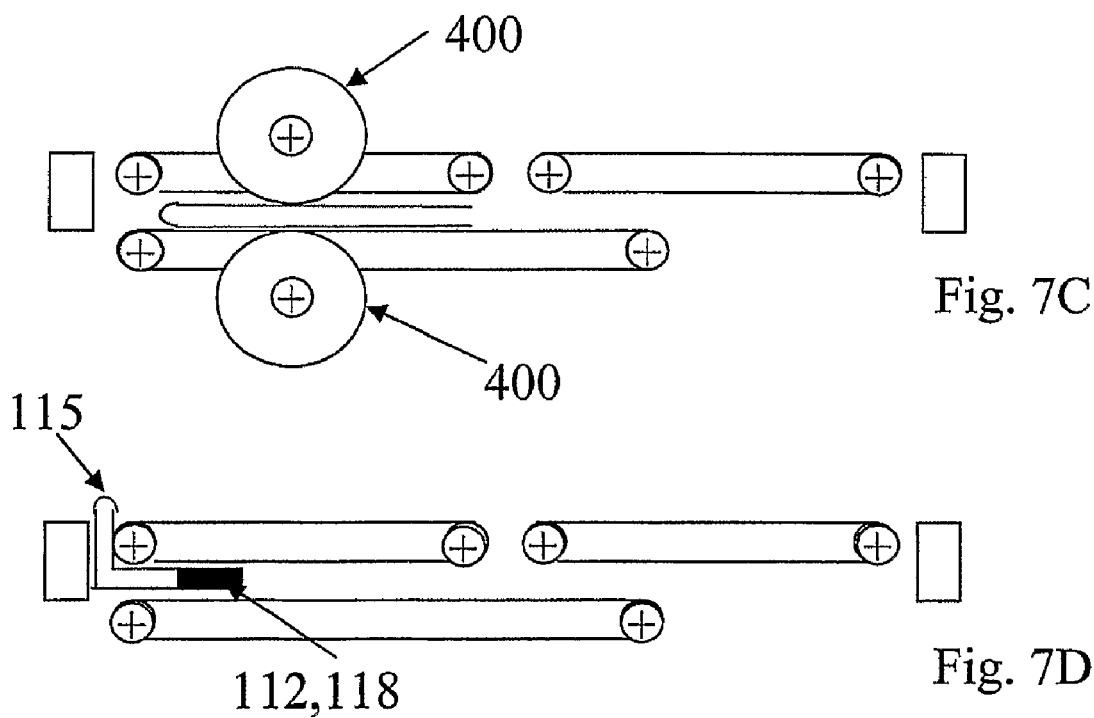
Fig. 7C
Fig. 7D
Fig. 7

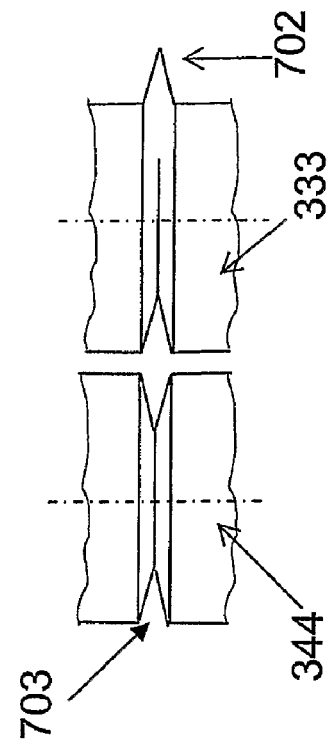
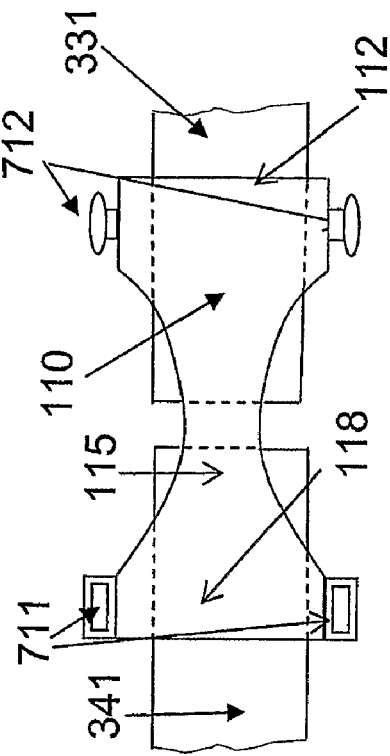
Fig. 8D
Fig. 8E
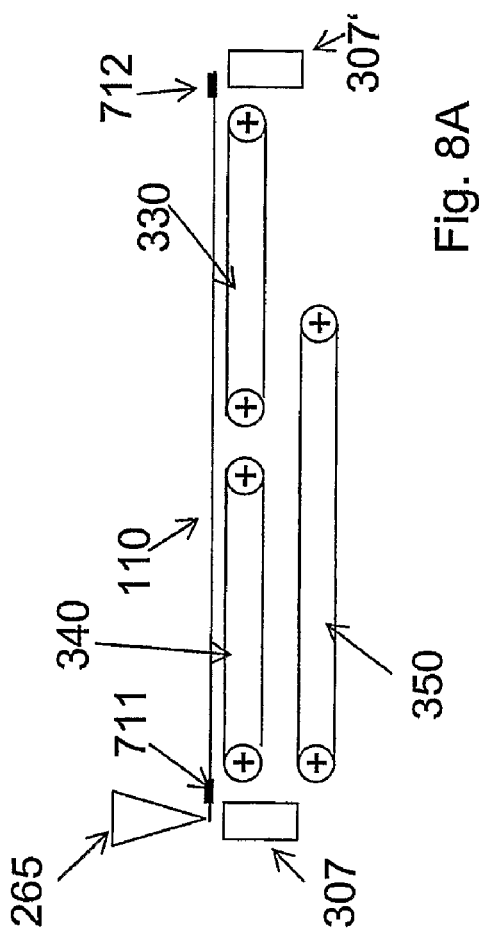
Fig. 8A
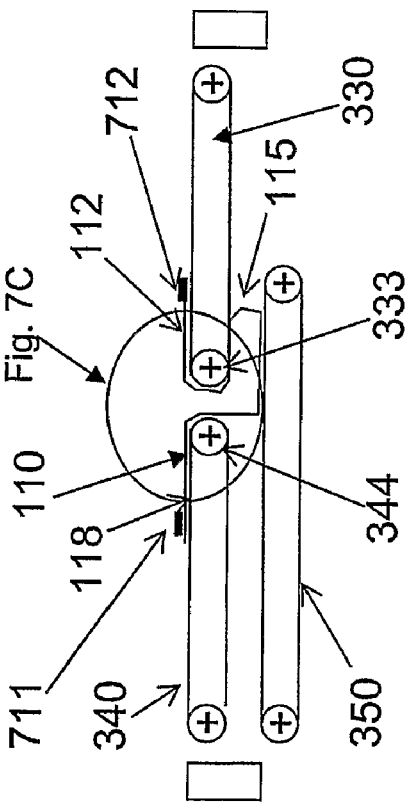
Fig. 8B

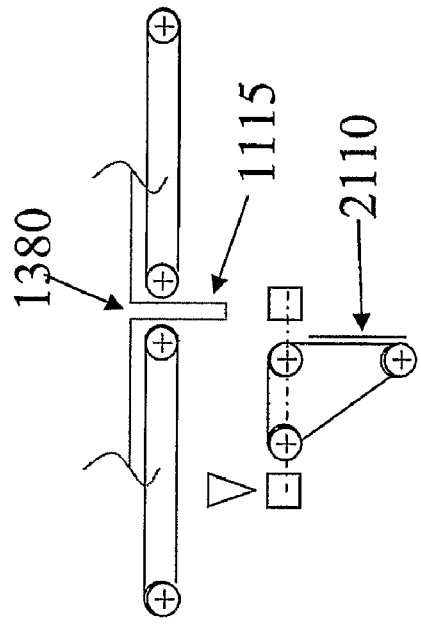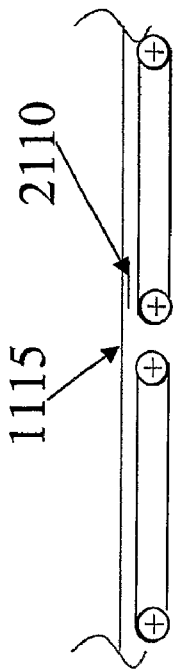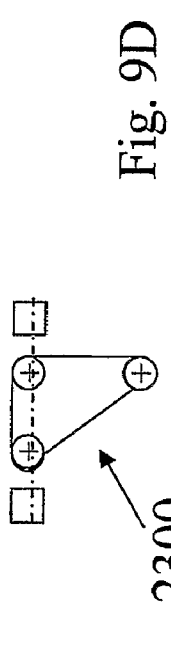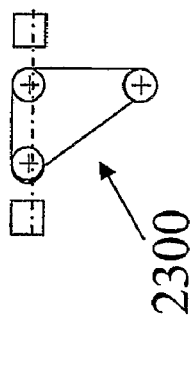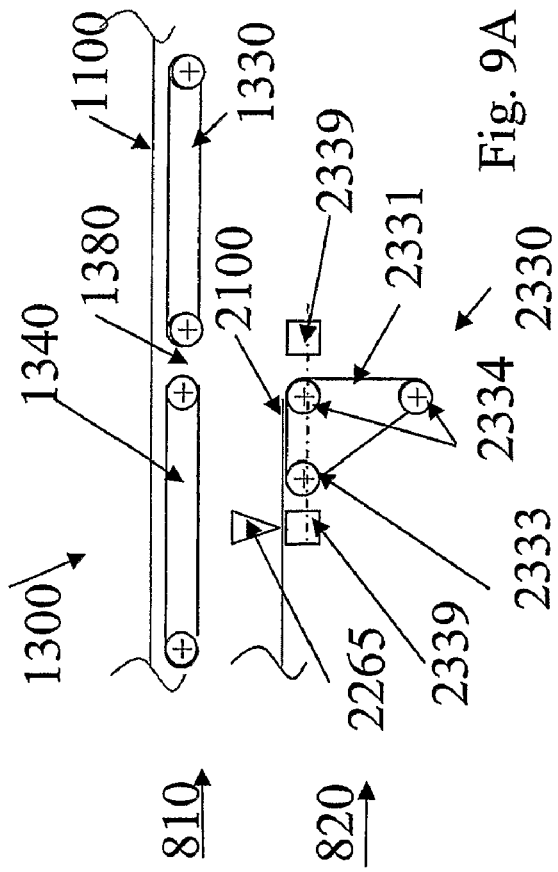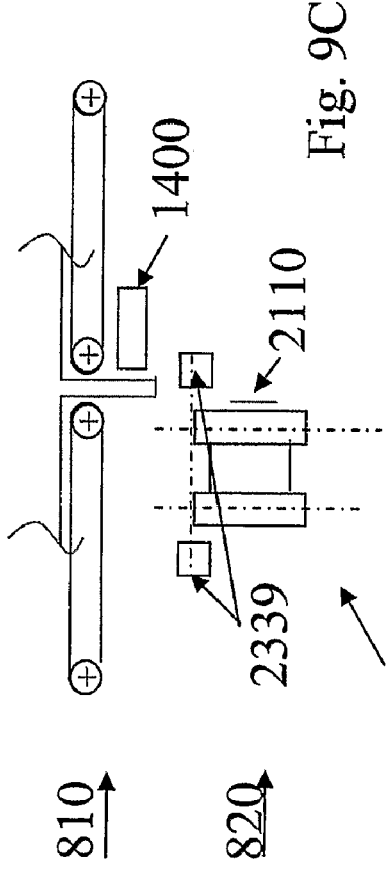
Fig. 9 A-D

Fig. 9E - H

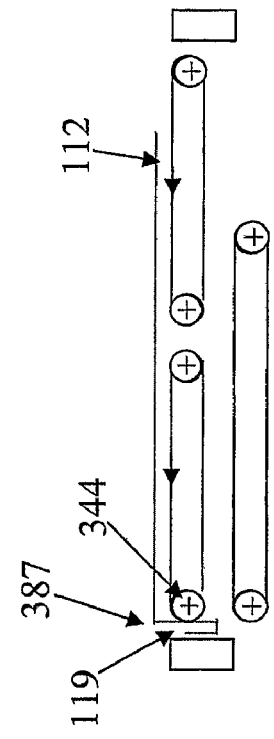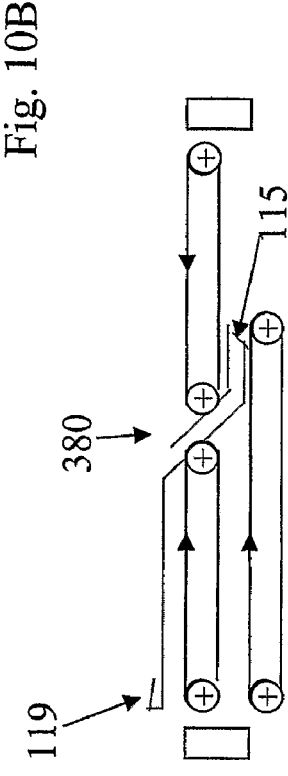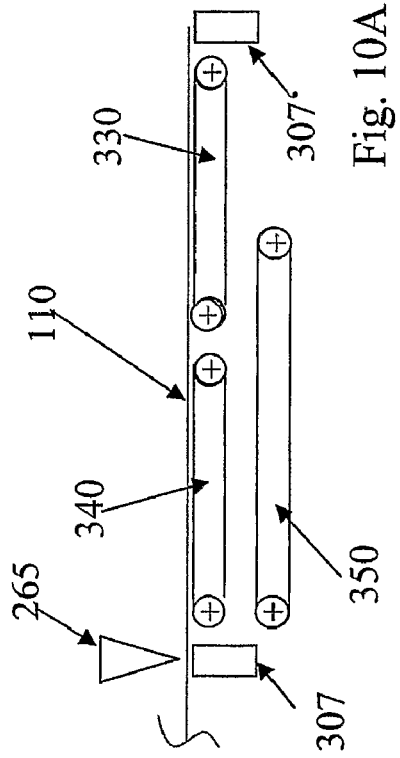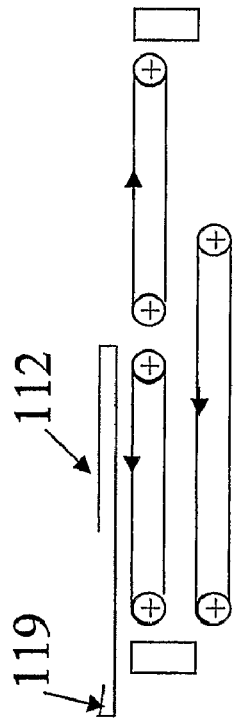
Fig. 10

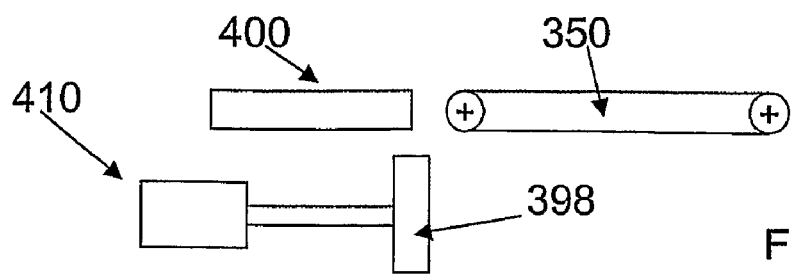
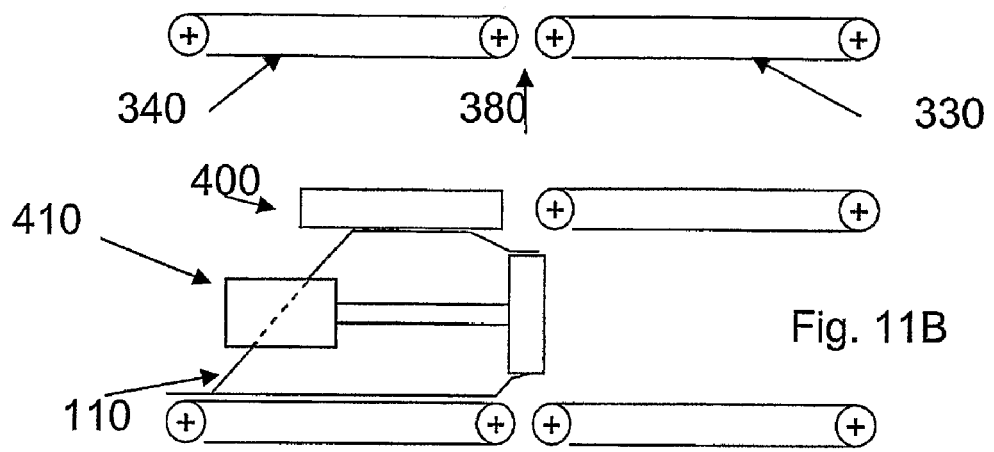
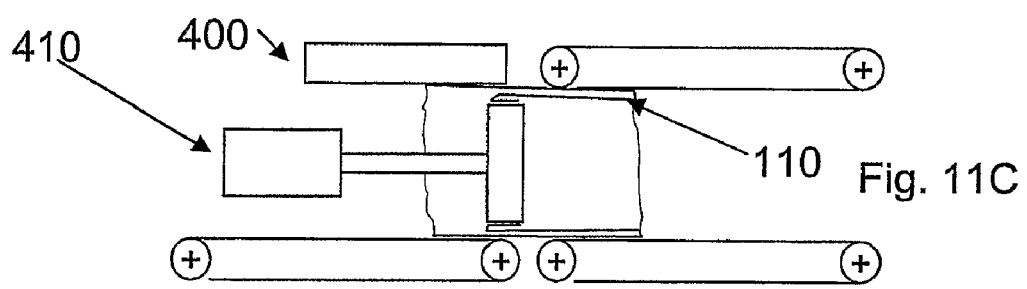
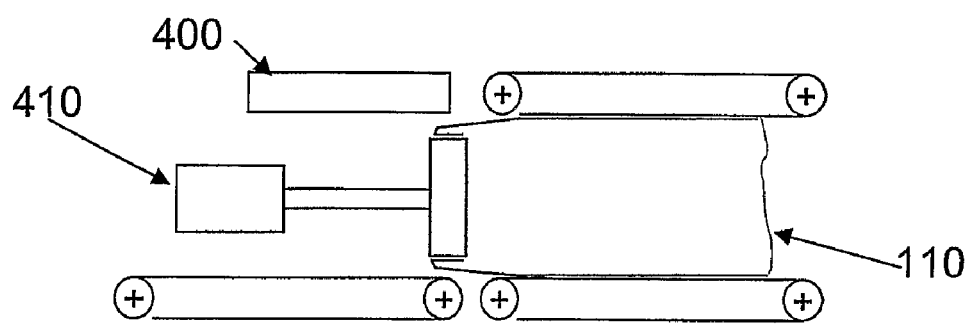
Fig. 11

WEB HANDLING PROCESS AND EQUIPMENT

CROSS-REFERENCE TO RELATED APPLICATIONS

This application is an U.S. national phase application under 35 U.S.C. §371 based upon co-pending International Application No. PCT/IB2005/000845. Additionally, this U.S. national phase application claims the benefit of priority of co-pending International Application No. PCT/IB2005/000845 filed on Mar. 29, 2005. The entire disclosures of the prior applications are incorporated herein by reference. The international application was published on Oct. 5, 2006 under Publication No. WO 2006/103487 A1.

FIELD OF THE INVENTION

The present invention relates to a method and equipment for the handling of web materials, such as essentially continuous webs of plastic films, textiles, non-wovens, or papers, or the like, or of parts or pieces of such webs. It also relates to modifying the movement of such webs materials, such as to allow other process steps to be performed on or with these web materials more easily. Particular aspects relate to the creation of a cross-directional fold in the web material and the combining of web materials with other materials.

BACKGROUND

Folding webs or articles which have a substantial extension in a length dimension along a fold line extending cross-directionally has since long been a challenge in a number of industry sectors, such as the textile sector, the hygiene or medical sectors, the packaging sectors, or the bookbinding/printing sectors.

Such cross-directional folds may be applied as such—so as to fold the web or piece or article for convenient packing. Folding of supple or delicate material, such as hosiery items, by means of a pivoting belt system has been described in U.S. Pat. No. 5,996,861. Cross-directional folding may also be a constructional feature and may impact the functionality of the article, such as in the case of disposable absorbent products, see e.g. EP-A-0254700, or in particular for so called "training pants", see e.g. U.S. Pat. No. 6,726,792.

Creating CD folds in a continuous web for attaching other materials thereto has been described in EP-A-0974323. Therein, a rotating wheel is disclosed, with individual plates forming the outer shell contacting the web. The segments are rotatably mounted about the axis of a circular path such that upon rotation of the wheel the distances between two adjacent plates change as well as the circumferential velocities of the plates vary between a minimum and a maximum value. In the described embodiments, this is achieved by affixing the plates to extendible and pivotable arms, all of which are affixed and rotatably mounted in the centre of a second circle offset the first circle. When a continuous web is run over the wheel by being affixed to the plates, the web will form loops when the gaps between the plates narrow and these loops will be pulled straight again when the gaps widen. This process allows for particular process steps to be executed on the web, such as attaching stretched elastics to the zones contacting the plates, but not in the zones being folded away. Cross-directional folding may also be used when forming a closed structure such as a pant-type article by combining parts of a web of an article to each other as described for example in WO-A-97/28709 in the context of producing underwear such as pants from non-woven material, or in U.S. Pat. No. 6,062,444, describing an arrangement for folding surgical gowns, or in EP-A-01120054 relating to disposable coats.

In the area of packing, cross-directional folds are used in so called festooning processes, such as described in US-A-2002/0046549, wherein a strip of material is packed by being folded in a zigzag fashion by means of a reciprocating carriage. In U.S. Pat. No. 5,144,787 the packing of articles of varying dimensions is disclosed, using an elevator type package wrapping machine wherein a film is wrapped around the article by means of an underfolder.

A folding machine for tri-folding a paper web is disclosed in U.S. Pat. No. 5,165,671, using a cutter drum with saw blade, a folding drum with saw blade receivers and folding blades, first folding drum and folding blades. Folding is further an important process step in the printing and bookbinding industry, such as described in U.S. Pat. No. 6,428,260, disclosing a first and a second adhesive edge are folded around the spine of a book by means of L-shaped clamp. In U.S. Pat. No. 5,876,027 a sheet bundle folding apparatus is disclosed, causing a bundle of sheets to be rolled into a pair of fold rollers thereby folding the bundle of sheets. The apparatus is provided with a drive source for rotating the pair of fold rollers in a normal direction to roll in the bundle of sheets and in a reverse direction to return the rolled-in bundle of sheets.

In all such sectors, it is desirable to produce at high production speeds, and henceforth also high transfer speeds of the webs, however, it should be noted that the presently applied techniques of folding parts or pieces of a web rely generally on a free movement of an edge of the web material (such as the leading edge, or the folding edge), see e.g. U.S. Pat. No. 6,669,618, where a disposable diaper is CD-folded and the end sections of the article are folded one on the other and connected to each other by means of a slot and tab fastener system. Any free movement of a leading edge, however, has the risk of inducing large variations with regard to positioning, and this risk increases strongly with increasing production speed.

The web speed during such process steps can be reduced without impacting the output of the productions system by using a means for splitting the web path so as to allow parallel working on parts, or pieces or sections of the web. Such web path splitting means can be a rotating wheel, such as described in U.S. Pat. No. 6,656,312. However, also such mechanical solutions pose speed limitations, as the rotatably moving shell segments need to be properly controlled in their acceleration and deceleration phase.

Such mechanical approaches also imply difficulties, when—as is often the case—process flexibility with regard to varying dimensions, and in particular varying length dimensions of the articles is desired. Not only is the available maximum folding dimension limited by the hardware design, but also the dimensions of the unfolded part of the web, or piece or part thereof are fixed for one set of hardware. Henceforth, when different sizes are to be produced, the complete hardware of the rotating wheel has to be exchanged.

The present invention provides in one aspect a solution to these problems. However, it further provides solutions to web treatment problems, which are hitherto unresolved, or which have been addressed so far by processes not involving CD-folding. This aspect refers in particular to web treatment process steps, which require a certain process time and a very accurate relative positioning of certain sections of the web or of pieces or parts thereof to other sections of the web or pieces or parts thereof relative to other materials, such as may be another web material. In this aspect, the present invention is particularly suitable due to the very controlled movement of the web material. This is achieved by submitting different sections of the web materials to a web section speed differing from the overall web path speed in absolute value and/or in direction of movement. This can be realized by a combination of a web support means (such as vacuum belts), and a drive means for the web support means (such as programmable drives such as servo drives). A web path splitting means (such as rotatable drums or wheels looped into the web path) allows parallel working on several sections of the web or on several pieces or parts of the web.

SUMMARY

The present invention is a method and equipment for handling a web material, which may be an essentially continuous web or an essentially continuous sequence of pieces of an essentially continuous web. The web material runs on a web handling equipment having a web path connecting a web supply means with a process section end point. The web material comprises at least a first and a second section, whereby the first section is oriented along the web path more towards the process section end point than the second section.

The method comprises the steps of a) providing a web material on a web supply means;

b) moving the web material from the web supply means towards the process end section along the overall web path at an overall web path speed $|v_0|$ relative to the frame of the web handling equipment;

c) providing a web path splitting means positioned along the overall web path and comprising at least a first and a second web handling section, each of these web handling sections comprising a section frame and a web support means connected to the section frame, having a surface which is movable relative to the section frame;

d) splitting the web path on the web path splitting means into at least a first and a second web sub-path, each running through one of the web handling sections; and transferring the web material along the web sub-paths to the web handling sections;

e) handling the web material of the web handling sections by 1) affixing the first section of the web material to the surface of a web support means in the initial contact region of the web support means without affixing a second section of the web material thereto;

2) changing the speed of the surfaces of the web support means, while having the first section of the web material remaining affixed thereto, thereby changing the relative speed of the first section of the web material to a second section of the web material;

f) thereby transferring at least parts of the web material out of the initial contact region of the web support means into an operating region of a web support means or of a further web support means;

g) optionally performing further web handling or treatment steps on the web material;

h) removing the web material from the web handling section;

i) providing the web handling section for repeated executions of the web handling steps d) to h).

The method can be used for forming a cross-directional fold in the web material, optionally for forming multiple folds, such as of the leporello or accordion type.

The method may further comprise a web treatment step, which can be a combining step, so as to combine different sections of the web material with each other or with other materials. The combining may be essentially permanent, such as can be achieved by gluing or welding, or the combining can be a releasable combining, preferably of the slot and tab or button type. The combining may also be of the combining of a web material with a secondary web material.

The method is particularly useful for the manufacturing of disposable hygiene articles or textile articles, or for packaging processes, or for handling or treating printed material.

In a further aspect, the present invention is an apparatus for handling such a web material, which comprises i) a means for supplying the web material and for transferring the web material towards a process section end point, thereby defining a web path for transporting the web material at an overall web path speed;

ii) a web path splitting means positioned between the web supply means and the process section end point for splitting the web path into at least a first and a second web sub-path;

iii) the web path splitting means comprising a web handling section for each of the web sub-paths for handling the web material;

iv) each of the web handling sections comprising a section frame and at least one web support means connected to the frame, wherein the web support means has or have a) a web support means surface for temporarily affixing a section of the web material to the web support means, b) an initial contact region and an operating region;

c) and a web support drive means for changing the speed of the web support means surface of the web support means relative to the frame of the web handling section, thereby moving at least a portion of the web material from the initial contact region into the operating region.

The web path splitting means may be a rotatably mounted drum. The web support means can have an essentially endless surface, preferably a belt, an electrical drive means, preferably an electrical servo motor, and a means for temporarily affixing the web material to the web support means, e.g. electrostatics, or mechanical fixation means, or preferably vacuum suction means. In a preferred embodiment, the web support means is a belt system, with an essentially endless belt, having a freely programmable electrical drive means integrated in a belt support roll. The apparatus may further be equipped with a helical screw feeder system adapted for receiving web material pieces for positioning of such pieces in a stack.

BRIEF DESCRIPTION OF THE FIGURES

FIG. 3A-D: Schematic diagram for handling a web by forming a non-permanent CD-loop;

FIG. 4A-D: Schematic diagram for tri-folding a web piece;

FIG. 5A-D: Schematic view of examples of multi-folded webs;

FIG. 7A-D: Schematic view of a process for web handling: side seaming;

FIG. 8A-E: Schematic view of a process for applying slot-and-tab fastener;

FIG. 9A-H: Schematic view of a process for applying cross-directional elastification;

FIG. 10A-E: Schematic view of a process for multi-folding cores of absorbent articles;

FIG. 11A-D: Schematic view of a process for inverting tubular elements.

DETAILED DESCRIPTION

Figure 1:
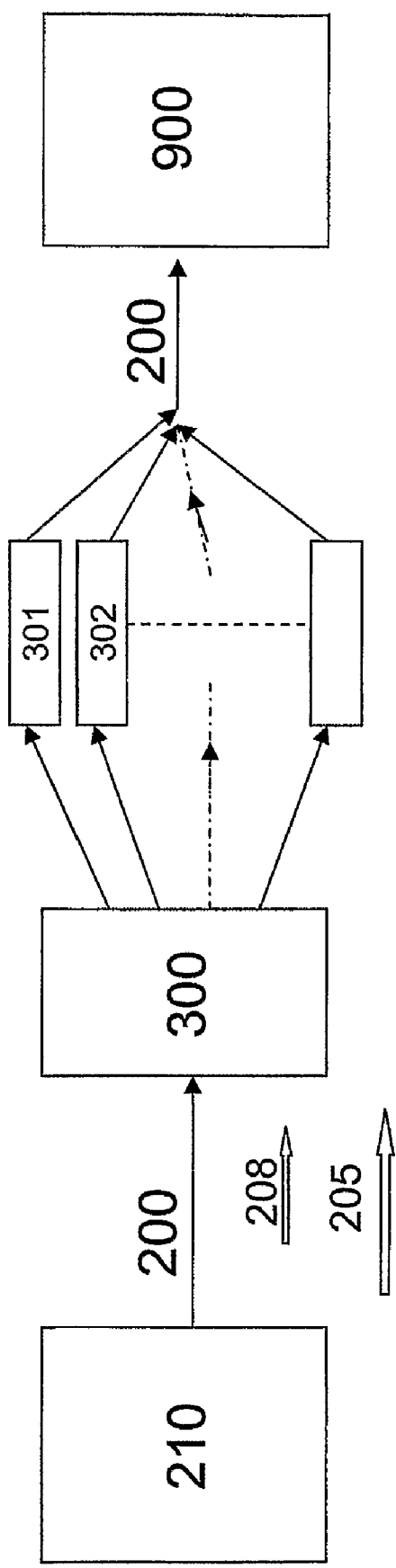
FIG. 1: Schematic process concept.

The present invention is concerned with web handling. Generally, the term "web" relates to any material which is essentially endless or continuous in one direction (generally denoted as "x-direction" or "machine direction"). Webs are often, but not necessarily, stored, supplied or used in roll form and thusly also sometimes denoted "roll goods". Whilst these are then not "endless" in the strict sense of the word, their extension in this x-direction is significantly larger than in any other direction. By combining consecutive rolls or other batches, ("splicing") such webs can be considered "endless" for all practical purposes. Webs may be transported in a "batch" form, such as when a roll thereof is shipped, or they may follow a "web path", such as when the webs are unwound from a roll, as described hereinafter.

Often, but not necessarily, webs have an essentially uniform thickness (herein denoted as "z-direction", and also constant width (herein denoted as "y-direction") along the x-directional length. Webs may be of essentially uniform composition, they can be mixtures of materials, they can be composites of materials such as being layered (different materials arranged in a juxtaposed position in the z-direction) and/or can comprise stripes of different materials or materials having different or varying properties (i.e. arranged in a juxtaposed position in the y-direction).

Typical examples for webs are—without implying any limitation—plastic films or foils, textiles, non-wovens, nets, scrims, paper, or cartons.

Within the context of the present invention, the term web materials relates to continuous webs as described in the above, but also to parts or pieces of such an essentially continuous web, which form an essentially continuous sequence. When such continuous sequence is moved, it will form a "sequence path", which is also considered the web path. For example, if a an essentially endless or continuous web, which is moved along a web path, is separated into pieces by repeatedly cutting a certain length of the leading end of the web, the resulting sequence of cut pieces would then still be considered a web material, following a web path, which is a continuation of the path which the continuous web followed before it was cut. As web materials in the form or parts or pieces follow the web path, they still have an orientation along this web path, which may be changed such as in case of rotating the web material or parts or pieces thereof. The sequence and the orientation along a web path distinguish web materials in the form of discrete parts or pieces from "sheets" for which neither a sequence nor an orientation along the web path can be defined. Thus, if the discrete parts or pieces of a web material are moved into a unit where they are stacked one upon the next to form a stack or staple, it would not be considered a web material, but rather a sheet or an article, and the web path would end at the stacker.

Within the present context, the term "web sections" refers to topological regions of a web material, which are connected to each other and not separated or cut. Thus, for a continuous web, sections may be defined as regions being in contact with a certain web support means, or regions running through a certain apparatus. If the web material consists of a sequence of parts or pieces of a continuous web, these parts or pieces may comprise sections, which are connected to each other by belonging to the same piece or part, such as are front and rear sections of one web material piece.

Web materials are often supplied in roll form, referred to when the width of the web defines essentially the width of the roll, or on spools, whereby the width of the spool is larger than the width of the web, and individual layers of the web are positioned adjacently albeit possibly overlapping in their y-dimension. Web materials may also be provided in boxes in a "festooned" arrangement, wherein one layer is folded onto the previous one, either in a single "accordion" arrangement or comprising a y-directional offset between individual layers.

Web materials need to satisfy certain requirements relating their intended use, but they should further satisfy certain properties to allow or ease handling. Thus, webs should have a certain minimum integrity as well as bendability or flexibility, so as to allow handling. Webs may also need to satisfy certain properties to allow transportation thereof, such as certain minimum or maximum friction properties, porosities (i.e. resistance to fluids like gases when passing through), or electrostatic properties. Although any material does exhibit a certain inherent elasticity, webs are often referred to as "inelastic", when they are not intended to return to essentially their original dimensions after being significantly extended.

"Web handling" within the present context refers to operations done with or on the web material which are not the primary end-use but which aim at modifying the web respectively its properties so as to be better suitable for such end-uses or further web handling steps. A web material may upon such processes loose its identity and may—e.g. upon a combining with another material or web—become a part or portion of another web material, or any other material, such as discrete articles or sheets.

To exemplify this aspect, a part of a typical disposable baby diaper production is considered. Typical web materials for such applications are non-woven materials and plastic film materials forming the outermost materials of the final article (i.e. oriented towards the wearer and the clothing during the intended end-use, respectively). These materials are delivered in roll form, "handled" all along the diaper manufacturing machine such as by being combined to each other as well as with a multitude of other materials, still forming a continuous web composite.

A further typical web material supplied to this process in roll form is a material having a looped surface designed to engage with mechanical fastening materials ("hooks") to allow closure of the finished article by the user. This loop material covers only a relatively small area on the outer surface of the article, and thus a piece of the loop material is Cut off its supply roll and combined (e.g. by gluing) with the outer plastic film. Thus the web handling for this material comprises the unreeling, the delivery to a glue application, the cutting, and the application of the piece thereof to the plastic film. Now, the loop material is part of the overall composite already formed by the other web materials, such as the plastic film.

After all desired materials are added to the continuous web composite, individual pieces are cut off and undergo a folding step. As during this folding step the individual pieces still follow the web path in a particular sequence, the pieces would still be considered "web materials". Once, however, the folded pieces are combined to form a stack within a bag or carton, the web path is terminated, and the pieces are not considered "web materials" but rather articles.

For the present context, "web handling" refers to operations not relating to the intended end use of the web materials, and may include web treatment steps and combining steps. Continuing the example of the production of baby diapers comprising hook and loop closure elements, these may be attached to each other during the manufacturing process so as to form a "pre-closed" diaper, e.g. during or after the folding step. In the present context, this would be considered to be a web combining step and thus a web handling process step. If, however, the combining with the hooks were to be done by the end-user (e.g. upon application of the diaper article to the baby) it would not be web handling within the context of the present invention.

Apart form such combining steps, web handling within the context of the present invention may also include treatment of the web, i.e. subjecting the web or parts thereof to conditions which temporarily or permanently change a property or the dimensions or the position thereof.

A change of properties, such as density, permeability, integrity, surface roughness, and so on may be achieved by any suitable operation, such as mechanical action, heating or cooling, inducing chemical reaction, submitting to irradiating or other actions. It may also encompass the combining with other materials, such as by spraying, coating and so on. A change of dimensions can be achieved by operations like cutting, pressing, stretching and so on. Generally, such operations are also referred to as "converting" steps, e.g. modifying a raw material to a final product, but also when creating or using a "semi-finished" or intermediate product.

The change of position of a web relates to the change of position of certain sections or pieces or parts of a web. This shall be explained by considering a web being unwound from a first roll for being wound onto a second receiving roll, both rolls being connected by a fixed frame of reference. Considering any particular points on the web, these define, when moving from the first roll to the second under steady state conditions, a certain path, referred to as the "web path", thereby further defining the "overall web speed", i.e. the speed at which any point of the web travels along this path. The overall movement of the web respectively points of the web along the web path also defines an overall orientation, here being from the first to the second roll, sometimes also referred to as "downstream". Following the distinction of "raw material" and "converted" material, the overall process direction is from the raw material to the converted one, however, the web can follow this overall process in very divers directions, orientations, or speeds.

The web path does not need to be a straight line relative to the fixed frame of reference (here as being described by being set by the frame holding both the first and second roll) from the starting point, generally denoted the supply point, to the endpoint, which may be the endpoint of a complete converting process, or which may be more generally the endpoint of a particular converting section, i.e. the process section end point. The web path can be curved (e.g. when running over a roll or drum having its rotating axis essentially parallel to the y-direction of the web), it can a combination of curved and straight sections (such as if several of such rolls are in an offset arrangement along the web path) and so on. Such "web path deviations" may be out of a plane as defined by x- and y-dimension of the web, i.e. generally referred to as "up" or "down", and may also revert the overall direction (i.e. have an opposite orientation). The web path deviations may also change the overall orientation (i.e. relative to the frame of reference), such as when deviation rolls are arranged at an angled position relative to the web path. Thus, if this axis is arranged in a plane parallel to x-y-plane of the web but at an angle of 45° to the web speed orientation, the web path will make a 90° "turn" to the right or left (if leaving the "deviation roll" also in a plane parallel to the original x-y-plane).

When the web material comprises discrete pieces or parts travelling at the overall web path speed, certain operations may accelerate each of the pieces for a short period, after which the pieces may travel at a constant web speed again but now being spaced apart (obviously requiring some support, such as another web, or a support means such as transport belt or a support drum). Other operations may accelerate or retard only certain sections of the web materials, thereby inducing strain on the material, which may elastically or plastically elongate the total web, or pieces thereof, or sections thereof. In such process steps, the "front" (or "leading") section of a piece (i.e. the part which is further "downstream" along the web path) may travel with a speed which is higher than the "rear" (or "trailing") section.

A cut piece of a web may change its orientation, such as when being turned around its z-axis. Then it may continue to move along the original web path (but now the former side portions would present the trailing and leading edges), or also change the orientation of its path.

Often, it is desired to submit webs, parts or sections thereof to process steps, which require certain process time. Such process steps may be—without any limitation—printing, stamping, or combining operations like glue fixation or welding. If, for example, a web material should be cut or stamped, these process steps will require a certain time, which may be in the order of magnitude of several milliseconds. If the web materials have an overall web speed of 10 m/sec, the web will travel during the time required for the cutting or stamping several centimeters. If such a movement is not acceptable, the tools, with which the operations are executed, may be movable, such that the relative speed differential can be reduced, or even eliminated.

A further known approach to this problem is the use of web path splitting means, i.e. the web path is split into individual sub-paths on which several essentially identical process units may be operated simultaneously, but which are operated at different stages at a given time. This may be achieved by a track switch distributing subsequent parts or pieces of a web material to N parallel web paths, where the individual web path speed is reduced by a factor 1/N of the overall web path speed. After the process steps have been executed, the individual web paths may be joined to form a single web path, travelling at the overall web path speed. Such approaches do, however require significant space, which is often not available in production units.

An alternative to such a track switch approach uses wheels or drums designs. As disclosed in U.S. Pat. No. 6,656,312, a hexagonal drum comprises six parallel web handling sections for executing all the same (and only) process treatment step. The time gained by this approach will depend on the number of parallel units in a similar relation as for the track switch approach.

Similarly, when using an apparatus as described in EP-A-974323 as already discussed in the background section, the looping and folding of the web between two adjacent shell segments or web support plates will allow a certain extension of the treatment times on the unfolded parts of the web, however, mostly due to mechanical limitations of this design by not more than about 30%. This process changes the local web movement speed in superposing sinusoidal speed changes to the overall web speed.

Generally, web handling processes include the web transport means for holding and/or driving and/or (re)orienting the web(s). Typical equipment elements for such web transport means are rolls, drums, belts or bars, whereby the webs may be run in direct contact over their surfaces. Thereby, the relative speed differential between the surface or the transport means and the web can be essentially zero (e.g. the roll or drum or belts having a tangential surface speed equal to the web speed), it can be equal to the web speed (e.g. in case of fixed bars) or it can be any desired relative speed.

Any of the rolls or drums may drive the web (such as by being driven by a motor) or retard the web (such as by having a brake function), and/or deviate the web path (such as deviation bars). The contact may be friction dominated (such as when using rubber rolls if higher friction is desired, or steel bars if low friction is desired), or other process steps may be taken to impact the contact as desired.

The present invention aims at providing novel process concept and the corresponding equipment for handling web materials as well as more specific applications in various technology fields. To this end, the development includes the equipment as described herein below arranged so as to enable the respective process steps. In the following, the present invention is explained using a particular arrangement, such as might be useful in the production process for disposable absorbent articles. It will be apparent to those skilled in the art and will also be further detailed herein below, that it can be applied to many different uses. Thus the reference to certain specific aspects such as shown in accompanying figures should not be considered limiting in any way.

Unless otherwise stated, the figures are schematic representations of the technical elements in a cross-sectional or side view of the equipment. Equal numerals in various figures refer to the same features or elements.

FIG. 1 describes very generally the process concept by depicting a web supply means 210, from where a web material is transferred along a web path 200 towards a web path splitting means 300, which divides the web path into parallel sub-paths running through a number of web handling sections 301, 302, . . . . The sub-paths may be combined again to form the common web path 200, along which the web material will reach the process section end point 900, from where it may be taken to further process sections or where the web handling process may end. The arrow 208 denotes the overall web path speed on the web path 200, and the arrow 205 denotes the overall web path direction, here from left to right and from the web supply means towards the process section end point.

Relating to FIG. 2, the explanation refers schematically to an exemplary process of cutting and folding a web material in the form of cut pieces of a continuous web cross-directionally (i.e. along a fold line across the width of the web materials).

Figure 2A:
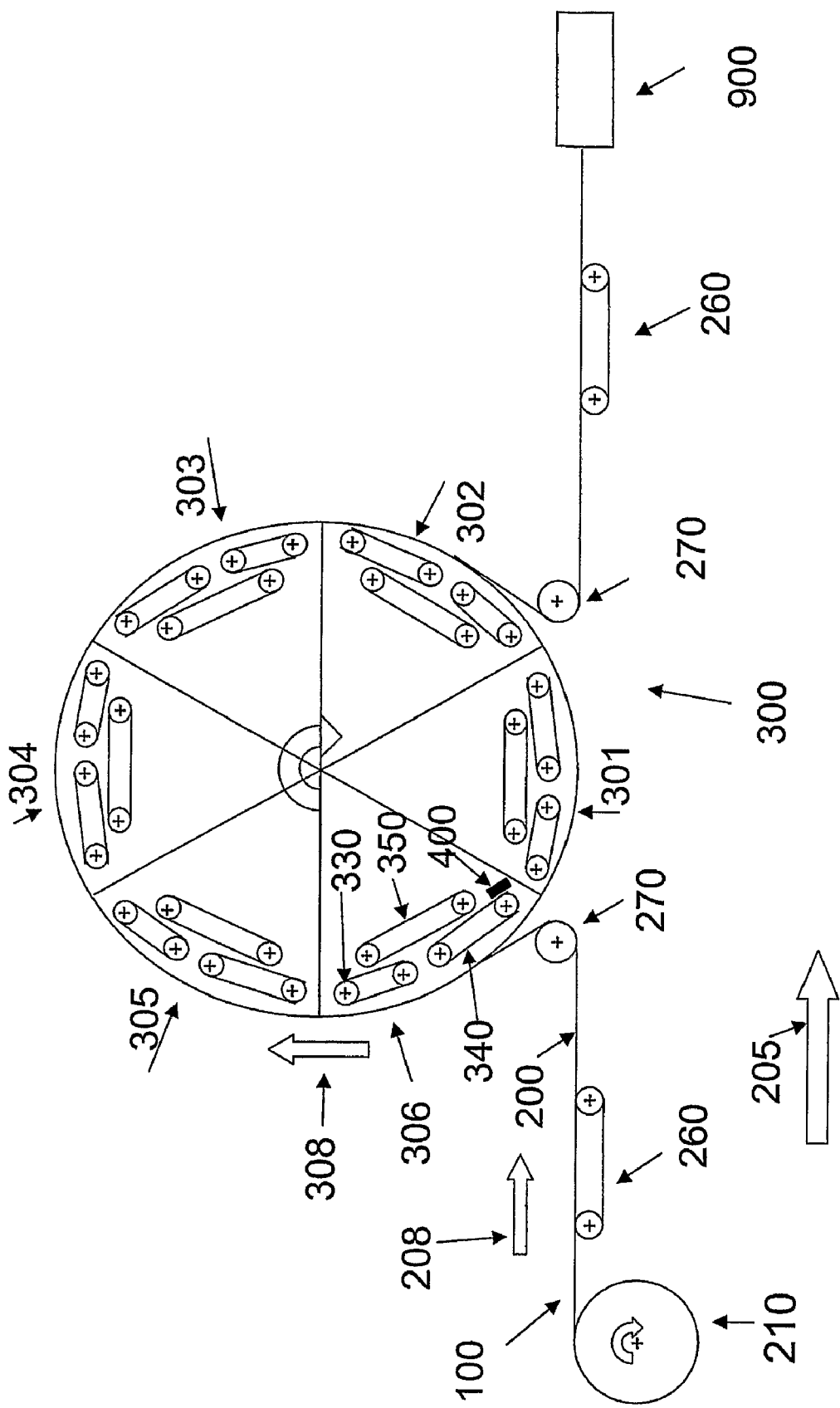
FIG. 2A: Schematic equipment outline.
Figure 2D:
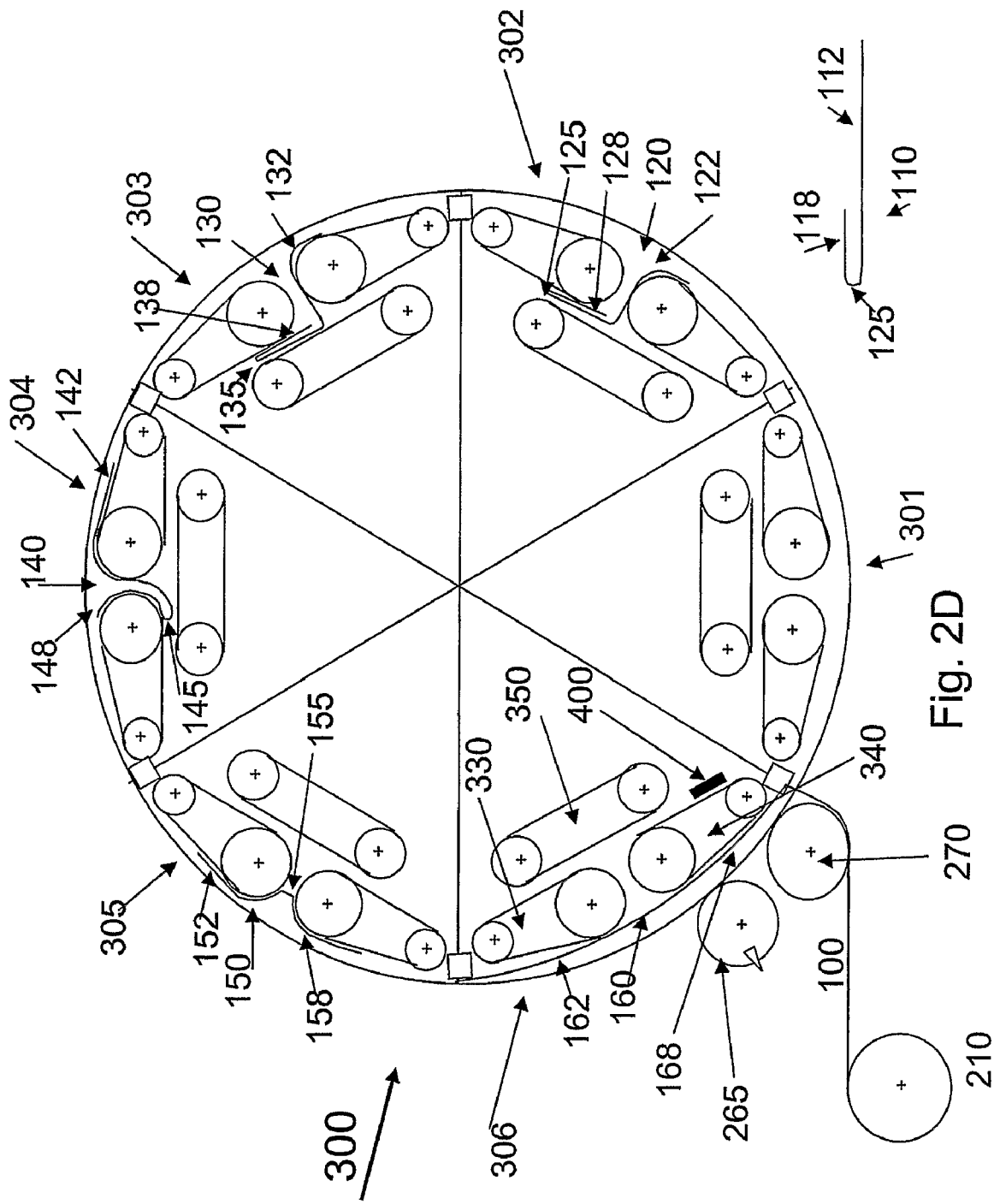
FIG. 2D: View of an equipment as in FIG. 2A including web material.

FIG. 2A shows the equipment detailing the key equipment features, especially the web path splitting means here in the form of a rotatable drum or wheel 300. An exemplified web handling section is shown in an enlarged view in FIG. 2B in form of a drum segment 304. FIG. 2C shows in an enlarged view a web support means 330. FIG. 2D shows more details of the web path by depicting several of the web pieces as these move through the process.

Thus, the exemplary process comprises the following steps using the following equipment:

1) Providing an essentially continuous web material 100, being moved such as by web transfer means 260 from a web supply means 210 along a web path 200 at an overall web path speed $|v_0|$ 208 towards a process section end point 900.

2) Providing a web path splitting means 300, here a rotatable drum located along the web path 200 between the web supply means 210 and the process section end point 900, mounted such that the web path could run over the outer surface of the drum. Drum 300 comprises a predetermined multiple set (here six) of essentially identical web handling sections 301 to 306 located towards the outer surface of the drum. The equipment may further comprise a web guide means 270 to direct the web to and from the drum, and a web separation means 265, which may be a rotating knife, to separate the continuous web into consecutive web pieces 110, 120, 130, . . . .

3) Providing each of the web handling sections 301 to 306 with one or more web support means, here shown three web support means 330, 340, 350 (in FIGS. 2A and 2D, these are indicated for each of the sections, however, the numerals are only given in one section). In the present explanation, web support means is exemplified by a vacuum belt system comprising a belt 331, 341, and 351, a vacuum box 332, 342, and 352, a freely programmable belt drive support roll 333, 343, and 353, a free support roll 334, 344, and 354 and being operated at respective web support means speed 338, 348, and 358. The web support means are connected to the web handling section and hence to the drum by a section support frame, not shown in the figures.

4) Directing the web material 100 from the web supply means 210 over a web guide means 260 into the web path splitting means 300 and after separation by web separation means 265 onto a first web support means 330. As the drum rotates with a tangential speed $|v_{Dr}|$ 308, which without any changes of the web support means speed $|v_i|$ corresponds to the overall web path speed $|v_0|$ 208, the cut pieces will be held by the vacuum suction means 332 onto the belt 331. The belt 331 may move at the time of transfer with a web support means speed $|v_1|$ 348 relative to the section support frame. Thus the web is received on the web support means 330 in the initial contact region 335 (see FIG. 2C). This region can be readily visualized, if it would be assumed, that when the drum 300 were stationary (i.e. $|v_{Dr}|$ (308)=0), and the continuous web would run over the individual stations at the overall web speed $|v_1|$ (338)=$|v_2|$ (348)=$|v_0|$ (208) without any speed changes. Then, all web support means 330, 340, which are positioned outwardly so as to then contact the web, would contact the web in the initial contact regions 335, 345, . . . . The remainder of the surface region of the web support means will then correspond to the operating regions 336, 346, 356. These are regions, through which the web will travel, if any of the relative speeds will change as explained hereinafter. A web support means not positioned towards the outer circumference of the drum, such as depicted here for web support means 350, will have no initial contact region, but all these web support means will have an operating region only. It should be noted, that these initial contact and operating regions are stationary relative to the web support means. If, as will be described hereinafter, a web support means changes position and/or size or shape, the primary and secondary regions may change accordingly.

5) Temporarily affixing the web pieces 110, 120, . . . to the surfaces of the web support means such that the web can follow any change of speed $v_{1,2}$ (338, 348) of the web support means. Considering the set up as outlined in FIG. 2, a first (leading) section of the web material 112, 122, 132, . . . will be affixed to the first web support means 330 in the various web handling sections 301, 302, . . . . The second (trailing) sections of the web material 118, 128, 128, . . . will be affixed to a second web support means 340 in the various web handling sections 301, 302, . . . .

6) Changing the relative speed between the speed $|v_1|$ 338 of the first web support means 330 and $|v_2|$ 348 of the second web support means 340, thereby creating a speed differential between at the front section 112, 122, . . . of the web pieces and the trailing section 118, 128, . . . e.g. by retarding the leading section 112, 122, . . . relative to the trailing section 118, 128, . . . thereby creating a loop in the central section connecting the first and the second section 115, 125, . . . of the web material in the gap 380 between the first and the second web support means 330 and 340.

7) The loop may optionally be caught by a third web support means 350 so as to further minimize free slack and to ensure proper web control and guidance.

8) Optionally applying further processing or converting steps on the web material while or after the loop has been formed and/or further processed. In FIG. 2B this is exemplified by a combining tool 400 positioned between the first and third web support means, 10) Removing the web materials from the web path splitting means and guiding it such as via web guide means 270 to the process section end point 900.

FIG. 2D focuses on the web material as it travels through the process, starting from the web supply means 210 as a continuous web 100 via a first web transfer means 260, and a web guide means 270 to the first web handling section 301, where—in the current exemplification—it is cut into web pieces 110, 120, etc. Upon rotation of the drum—in the present example clockwise—the next piece of the web material will be fed into the following web handling section, whilst the first one is processed. For ease of representation, FIG. 2D shows a snapshot with six pieces of the web material being fed into the web splitting means, such that web cut piece 110 has left the station already, and the pieces 120, 130, 140, 150, and 160 are being processed in the respective web handling sections 301 to 305 (station 301 is shown empty). The handling can be followed when following the overall web path direction 205, which is used to generally describe the movement of the web from the web supply means 210 to the process section end point 900.

The first web handling action is shown for web material 100 in web handling section 306, where the cutting or separation means 265 separates a piece from the continuous web 100. The web cut piece first contacts the first web support means 330, and upon further rotation of the drum 300 also the second web support means 340, where it is shown as web cut piece 160 overlaying both web support means in their respective initial contact regions 335 and 345 respectively. When the drum 300 rotates at a speed such that the tangential speed corresponds to the overall web path speed, the first and second web support means speed can be zero. As shown for web handling section 305 with web piece 150 with first section 152 and second section 158, the relative speed between the first and second web support means 330 and 340 is changed, here by either moving the first web support means 330 backward (relative to the overall web path direction), or the second web support means 340 forward, or both. Thereby, at least parts of the web material—here the central section connecting the first and second section—are moved from the initial contact region into an operating region, here by forming a loop 155 as shown in the web treatment section 305. This loop is shown more developed for the web handling section 304, now denoted with loop 145 folding into the gap between first and second web support means. In the present example, it is caught by third web support means 350, travelling at a third web support means speed 358, which may correspond to the speed of first and second web support means and a direction so as to move the folded loop away from the gap between the first and the second web support means.

At that point, the creation of a cross-directional fold has been achieved, as can be seen in FIG. 2D in web handling section 303 for web piece 130, at the beginning of the fold, and web piece 130 when the fold has further moved on the third web support means 350. It should be noted, that the leading and trailing sections of the web do not need to have the same length, as indicated in the figure.

The folding of the web can be the main purpose of the process. Optionally, other process steps can be performed, such as indicated by optional process equipment 400, which may be positioned at any suitable place so as to interact with the web material, respectively with certain sections thereof. As exemplified for web handling section 302, the process step 400 can be actuated when the web piece 120 is in its folded state, and the treatment step can comprise a gluing step so as to glue front or rear sections 122 and 128 or regions thereof to each other whilst being folded and hold on third web support means 350, or any other suitable bonding process step to connect respective regions essentially permanently or temporarily.

After the desired process steps are executed on the web materials, these can be removed from the web path deviation means, here exemplified for web cut piece 110, shown as being transferred via a web guide means 270 and a web transfer means 260 to the process section end point 900, along a common web path from where it can be further processed, or packed.

This example also indicates the benefit of an extended processing time as may be allotted to the optional process equipment 400. Without employing the web path splitting means, the time available would be directly influenced by the overall web path speed. By applying the web path splitting means with six parallel web handling sections, the time is increased by about a factor of six, and the use of the independently moveable web support means further widens the time window significantly.

Figure 2E:
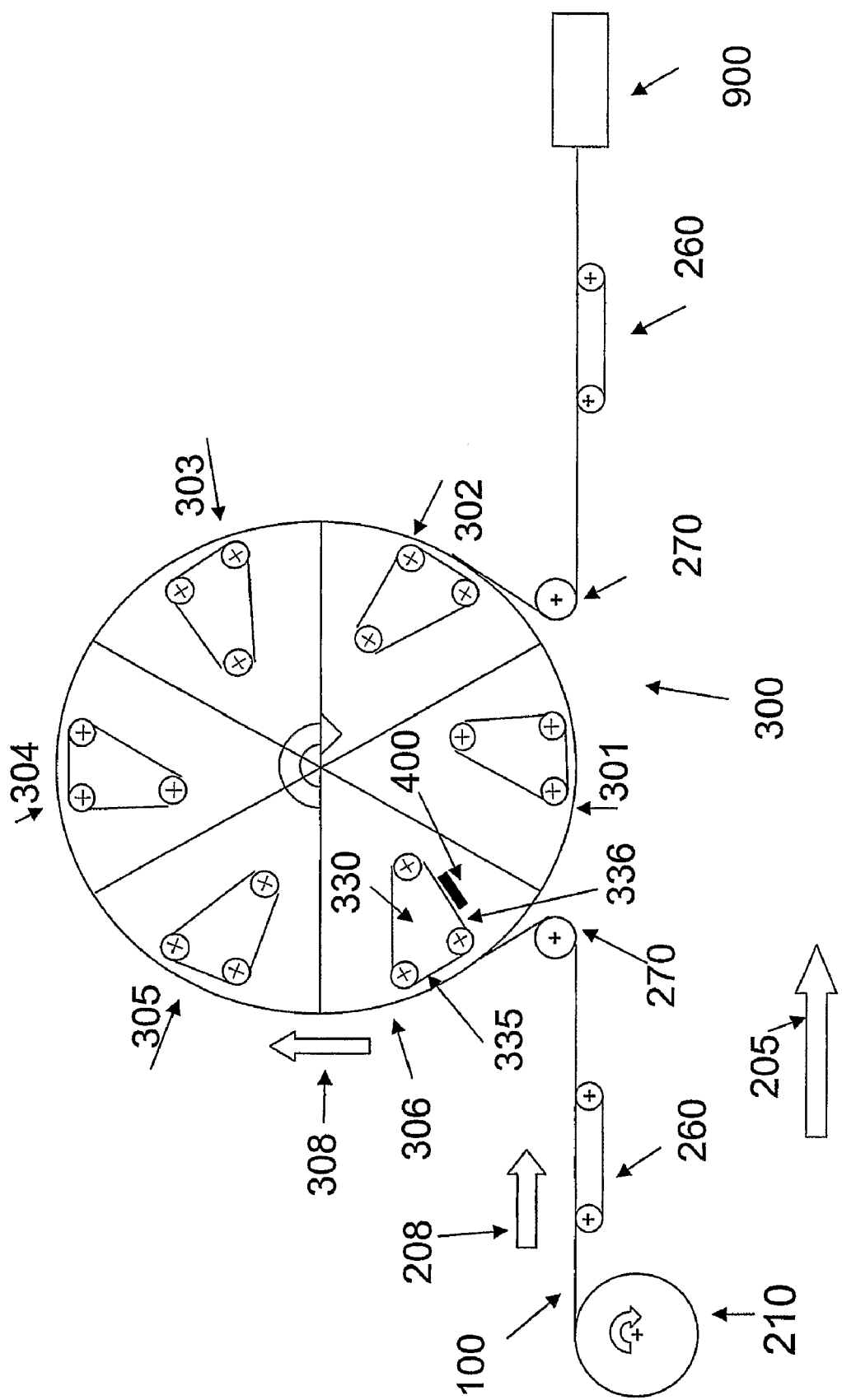
FIG. 2E: Enlarged view of a web handling section for the case of only one web support means per web handling section.

Instead of the three web support means as used for the above description, it is sufficient if each web handling section comprises only one (first) web support means (330), as illustrated in FIG. 2E. If the speed thereof is changed relative to the overall web path speed, such as being decelerated ($|v_1|<|v_0|$), a loop will form upstream of this web support means, and may be controlled by appropriate design of the web support means, which may, such as indicated in FIG. 2E, comprise a further belt drive roll, such that the belt may run on a triangular path. The initial contact region 335 is oriented facing outwardly and the operating region 336 rectangularly thereto. The loop may form in the operating region of the web support means 330, where it also may be treated such as by a treatment means 400.

Figure 2F:
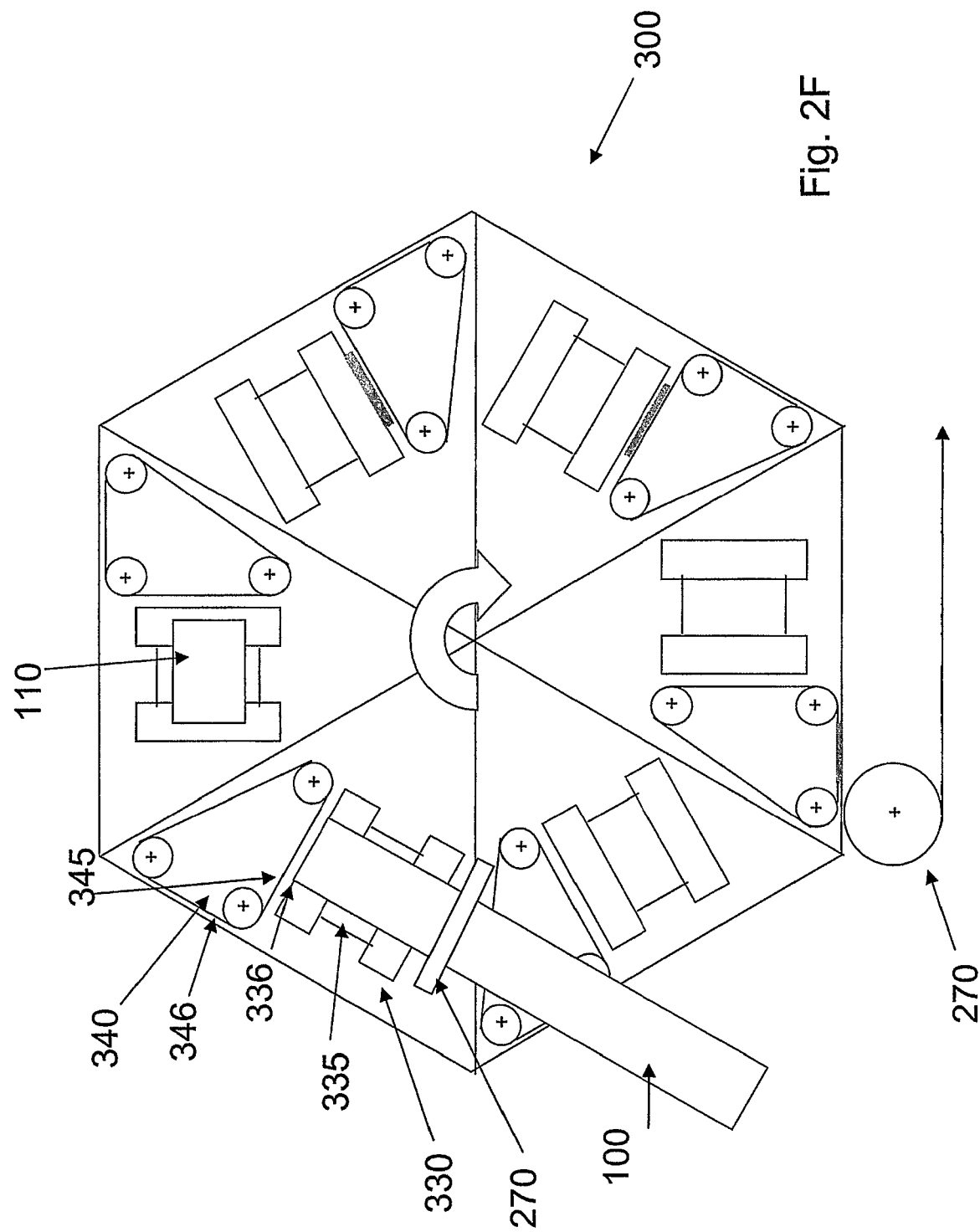
FIG. 2B: Enlarged view of a web handling section of FIG. 2A.
FIG. 2C: Enlarged view of a web support means of FIG. 2A.

In the above description, the web splitting means is essentially drum shaped, and the web materials are supplied thereto essentially tangentially or radially, i.e. the longitudinal direction of the web as being fed to the web splitting means is perpendicular to the longitudinal axis of the drum, and the x-y-plane of the web materials is oriented parallel to this axis. This however, does not need to be the case. FIG. 2F illustrates, that the x-y-plane of the web as being fed to the drum may also be parallel to the circular respectively hexagonal end planes of the cylindrical drum. This figure further shows a particularly useful application of the present invention, wherein the handling step is the turning of web material pieces, which may be fed to the web path splitting means 300 in this direction and orientation, where they may be received by a first web support means 330. The web support means rotates with the drum, while the web guide means 270 is stationary relative to the equipment frame. As the web support means passes by the element 270 the web material pieces are transferred. Optionally, the web support means 330 may be rotatably mounted around an axis perpendicular to their initial contact surface, so as to ensure straight transfer of the web pieces onto the support means. This first web support means is of similar design as shown in FIG. 2E, i.e. comprising a belt running over at least three support rolls so as to show a triangular shape. The initial contact region 335 is thus parallel to the plane of the drum, the operating region perpendicular thereto along the axis of the drum. Thus, after being repositioned by 90° on web support means 330, the web material or pieces thereof may be transferred such as by changing the vacuum suction of the respective web support means, to a second web support means 340, having the same or similar design as the first, but being affixed in a position turned by 90°. This web support means will receive the web material pieces in its initial contact region 345, and transport it to the operating region 346, from where it may be removed such as by a web transfer means 270, which may in this case also be a vacuum belt system, or a web with sufficient tackiness to securely take on the web material pieces. Optionally, the web support means 330 and 340 may be each connected to a separate web splitting means, which may be positioned adjacent to each other, and which may have a common rotational axis.

After having outlined the basic process principles of the present invention, the following will describe suitable equipment.

The web supply means can be any equipment for delivering a web. Thus it can be a roll, or a spool, a carton containing folded or "festooned" essentially endless material, optionally by including splicing equipment. Alternatively, the web material may come from another web treatment process step, or from a web forming step. Whilst the above description has explained the principle by referring to the web material being initially essentially continuous, there can be further process steps between the web supply means and the web treatment means according to the present invention. These process steps may include a separation step, such that the web materials can already be delivered as an essentially continuous sequence of web material pieces. These pieces may also be combined with other materials, which may be other web materials. Typically, these web pieces still have an extension in x- or y-direction significantly exceeding the thickness (in z-direction).

The web transfer means can be any equipment suitable for moving the web or its pieces or parts along the web path. Typical equipment is a transfer belt, a transfer drum and the like.

The web guide means can be any equipment suited to guide the web or parts or pieces thereof into the web path splitting means. Here too, belts or drums, rolls, or bars may be suitable.

The web path splitting means has the key task to allow multiple process steps to be executed concurrently on at least two web handling sections, thereby increasing the time available for the execution. A linear arrangement of the splitting means can be a switch similar to a junction plate whereby the web handling sections are arranged e.g. parallel to each other, be it adjacently in the y-direction, or the z-direction or both. In the latter case, the stations would form an array, wherein one element after the next is fed from a suitable web guide means. Similarly, the web handling sections can be arranged parallel in a circular relative position, like in a horizontal axis turret design. The more web handling sections are included, the more time is available for each of the processes executed on these stations. Web handling sections are preferably equal in design.

A preferred execution particularly suited for relatively high overall web speeds (see below) relates to a wheel or drum design having a number of repeating segments representing the web treatment sections. More segments allow longer process times without the need for reducing the overall production throughput. In a preferred embodiment, the number of the segments is an even number (2, 4, 6, . . . ) so as to ease mechanical design of the drum by avoiding out-of-balancing. The sides of the segments will extend from the centre of the drum radially outwardly towards the outer circular arc of the segment. This outer circular arc of the segment does not need to have the same diameter as the overall drum has, but it can have a larger one—and when this reaches infinity, the segment will have the form of a triangle, and the drum the form of a polygon. The outer surface of the segment can also be of any other form or shape, such as polygonal, or combinations of polygons with circle arc sections and the like.

The drum can vary widely in dimensions. The width can be the one of the web material; it can be the original length of a piece thereof, if this is rotated by 90° around an axis oriented in the z-direction. The width of the drum can be smaller than the web width, such as when the material exhibits a sufficient (CD-) stiffness, or other guide means are provided. The drum can also have larger dimension, such as when comprising further equipment for executing further process step. There can be two or more webs being run on a drum in parallel, or two drums can be operated to support a web. The diameter of the drum is essentially determined by general design principles (such as weight) and by the type and number of the web handling sections. A drum diameter can be 5 or even 10 times the width of the web material, or be more than about 2 m. The drum can be driven by any conventional drive means, preferably operating at a constant speed. Generally, though not necessarily, the cross-section of the drum will be symmetric to the centre point to ease rotation. Typically, though not necessarily, drums will be manufactured from metals like steel, aluminium or like, although also other materials such as synthetic polymers with or without embedded reinforcement structures, or ceramics may be used alone or in combination. The drum can be a closed drum, or it can be a frame onto which the respective elements, such as the various web support means, are mounted. Each section may have its own frame structure, or several or all sections may be connected to a joint frame structure.

Each web treatment section comprises at least one, typically not more than ten web support means. A web support mean can be any suitable means having an essentially endless continuous surface, which can be operated at variable and controllable surface speeds, and to which the web or pieces thereof can be temporarily affixed. If more than one web support means is utilized, these can be of the same design, or can have varying design. A first embodiment of a web support means is a rotatable drum or roll which can be driven by any programmable drive means or motor. In order to allow quick changes of the surface speed, the overall mass of the drum or roll should be reduced. A second embodiment for a web support means is a belt system, comprising an endless belt, which is run at least over a first roll, which is the belt drive roll, and a second, freely running roll. In certain applications of the present invention the web support means will not move constantly into one direction, but may be operated in a forward-reverse direction alternating mode. Then, an equivalent embodiment to an endless belt system is a discontinuous belt system, which may be driven by one or more programmable drive means over one or more free or driven support rolls accordingly, or programmable push-pull means (such as hydraulic cylinder arrangements) to move the belt forward and backward.

The web support means may be fixed to the web path splitting means, such as to the drum, or the frame forming the drum. The web support means may also be arranged to be moveable relative to the web path splitting means. Such a moveable arrangement may refer to the web support means as such, which may be moveable forward and backward (along the x-direction of the web path), upward or downward (along the z-direction of the web path), or sideways (along the y-direction of the web path). The web support means may also be pivotably arranged so as to change the angle such as relative to the x-y-plane of the web path. Also, if the web support means is a system comprised of a belt and support rolls, any of these support rolls may be moveable as to change the belt path. All rolls may have the same diameter, or different ones. A roll may also have an adjustable variable diameter. The web support means may also be moveable in any combination of these options.

The belt used for the web support means can be of any conventional transfer belt material, adapted to the specifics of the particular web. The properties of the belt can be such that the web material can be affixed thereto without any further aid, such as by friction. Preferably, the web support means further comprises a web holding means, such as mechanical clamps, or uses electrostatic effects, and the like. A preferred embodiment uses vacuum boxes arranged in certain sections of the web transfer means. The vacuum suction region can also extend to or include at least parts of the support rolls, thereby defining very accurately the points where the web materials will loose contact to the web support means.

The drive means for the web support means, i.e. the drive for the drum or for the belt drive support roll is preferably "freely programmable" which denotes in the context of the present invention, that its operating condition can be changed according to a predeterminable sequence. This can be achieved by using electronic impulses to change speed and/or orientation of the movement of the drive means, essentially at any point in time across the full operating window of the web support means.

Particularly suitable drive means are servo drives such as the Smart Motors™ SM1720 Series available from Company Animatics, Santa Clara, Calif., USA.

Such servo drives can be controlled by the number of turns as well as the angular position within one rotation, such as by providing over 2000 individual set points per one rotation. They also can be controlled for the speed they are operated at. They even further have a reproducible ramp up and stop profile. As a consequence, appropriate programming may allow very precise operation. Typically, the drives will be controlled by computer (sub-) units, which also may control other process steps.

Whilst such drives may operate at considerable surface speeds, they not necessarily have to operate at the overall web speed, as the web path splitting means increases the available web treatment times.

Such drives are available in many executions, but an important feature is the size which should be minimized so as to allow compact designs of the web support means but consequently also of the overall web handling apparatus. Particularly suitable executions are such that the drive mechanism, i.e. the motor, which is generally electrically operated and the control units, which are typically electronic elements, are designed into the core of the drive support rolls, or into the frame of the web support means.

The process concept of the present invention can be applied to a wide variety of basic web handling processes or elements thereof. Such handling processes can be "treatment steps", where the web materials as such is treated by certain actions, or "combining steps" wherein the web materials is combined with other materials, such as other webs. Of course, a process may comprise one or more of either or each of these steps. Other process steps not being part of the present invention may also be included and combined in a variety of combinations and permutations.

The most basic treatment step according to the present invention is a cross-directional folding of a web material. A CD-loop or fold may be formed permanently, such as by combining sections of either side of the fold to each other, as will be described hereinafter. It may also be temporary thus allowing for example slow process steps, such as further web treatment steps, to be executed during the deceleration period. Examples for such processes may include heating, irradiating or curing of materials and so on. A further application of employing temporary loops may be the treatment of web materials of varying length in one equipment without needing hardware adjustments. This is illustrated in FIG. 3, showing exemplarily only one web handling section of a drum (as otherwise shown in FIG. 1), with a first, second and third web support means 330, 340, and 350, respectively, and web separation means 265 and 265', the latter denoting the web separation means of the adjacent web handling section. The web handling section has an overall length 501, which is for a given drum. When web materials having varying web material length or sections thereof are to be treated such as indicated by web treatment equipment 400 in FIG. 3C, a section of the web material may be temporarily folded into the gaps 380 and 385 between first or second and third web support means respectively. Thus, the web is transported from the initial contact region 335, 345, 355 (as shown in FIG. 3A) to the operating regions as indicated with the loop in FIGS. 3B and 3C. After the process step has been executed, the fold may be released so as to extend the web material to its original full length and out of the operating regions 336, 346, 356, as shown in FIG. 3D. Similarly, web materials having a length less than the web section overall length, these can be positioned such that a part of the second web support means 340 is not covered by the web, such as indicated in FIGS. 3B and C, except, that there may be no loop formed in the gap 380.

Whilst an appropriately designed guiding means can function as a first web support means in this embodiment, such that only one further web support means will then be required, so as to form the loop between the web guide means (not shown in FIG. 3) and the first (and then only) web support means 330, it is a preferred embodiment to use a first and a second web support means. Even more, as in either of the options the loop may partially be unsupported and potentially move in an uncontrolled manner, it is even more preferred to "catch" the loop by the third web support means such as described in the examples hereinabove. This will widen the potential use significantly, as also web materials with properties which make it difficult to handle may be successfully treated even at high production speeds. The present invention is particularly beneficial when being applied to web materials having a low integrity or stiffness, which will in conventional processes tear or undergo uncontrolled movements.

The present invention further allows multiple folding, such as further exemplified in application embodiment No. 4 herein below. FIG. 4 schematically depicts a "trifolding" process, wherein a web material is folded twice to create three overlaying layers, by exhibiting only one handling section, with a first, second, and third web support means (330, 340, and 350, respectively). FIG. 4A shows the web material 110 initially extending over the initial contact regions surfaces of first and second web support means 330 and 340, in the present example such that about a third of its length is on the second web support means 340 and two thirds are on the first web support means 330. At that point in time, the transport direction of the second web support means 340 reverses, thereby transferring part of the web onto the operating regions of the first and second web support means, thereby forming a loop in the gap 380. The formation of the loop may be supported by a tucker means 390. When the web material contacts the third web support means 350, now travelling at the same speed as the other web support means into one direction, in FIG. 3B to the right, the loop will be transferred into this direction. When the leading section of the web material 112 is fully folded inwardly and transferred into the gap between the second and third web support means, both reverse their movement orientation, thusly pulling the longer trailing section 118 of the web material through the gap 380 into the gap 385 between the first and the third web support means, overlying the leading section 112, see FIG. 3C. When the web material is pulled in completely, the folding is finished, and the folded web material may be ejected, such as by a web guiding means 270, as indicated in FIG. 3D, or may be processed further.

Figure 6:
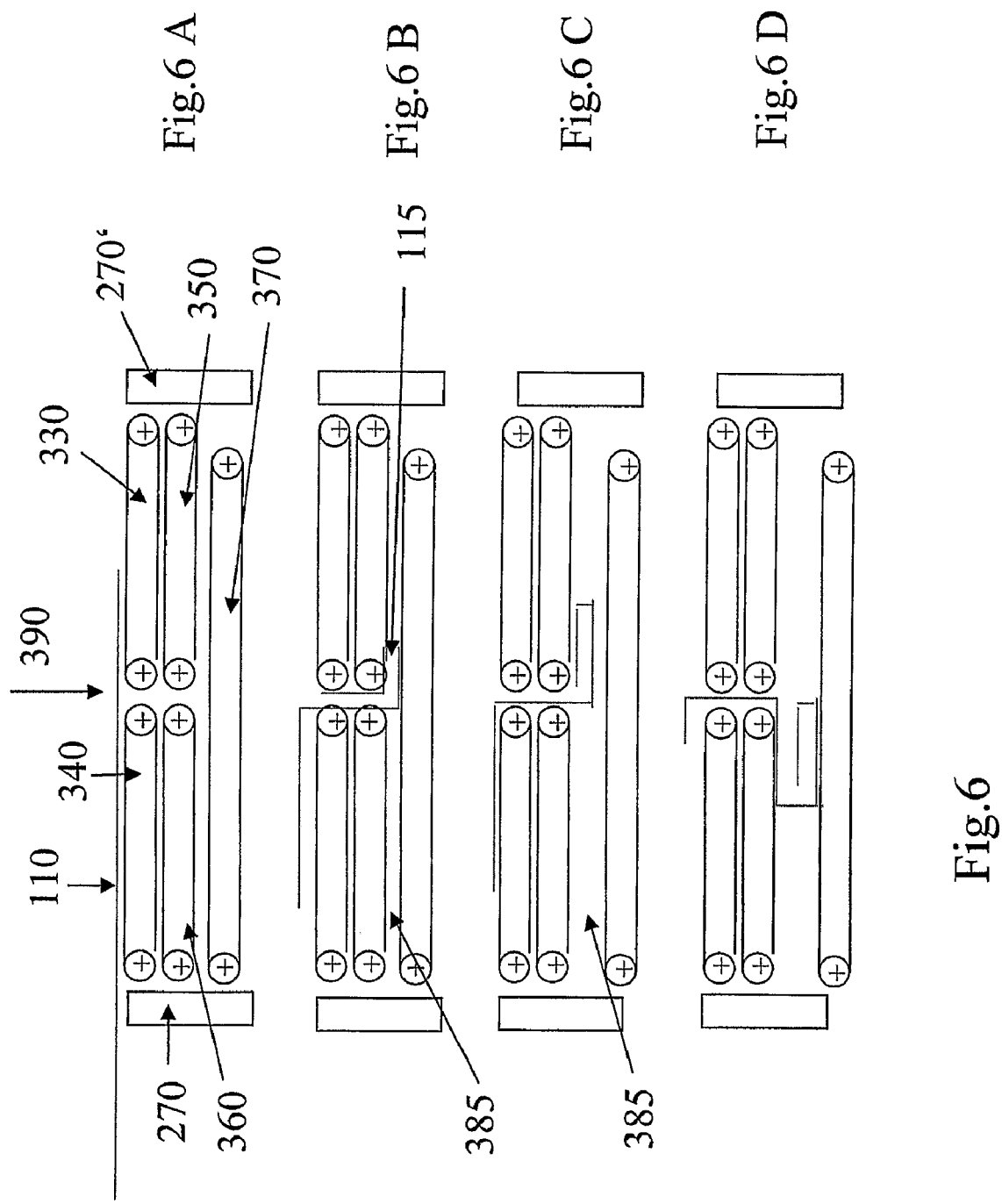
FIG. 6A-D: Schematic view of a process for multi-folding a web piece.

By appropriate selection of forward or rearward movement or stopping of the web support means, not only a trifolding, as shown in FIG. 5A, but also multiple folding can be achieved. Thereby, the end sections can be folded inwardly (or "e-fold" as shown in FIG. 5B) or outwardly (or "Z-fold" as in FIG. 5C). A process to achieve such folding is illustrated in FIG. 6, thereby using a set of five web support means 330, 340, 350, 360, and 370. Optionally, the width of gap 385 between the first or second and the third web support means may be adjusted to the increase of thickness. The result of such multifolds may look like "leporellos" or concertina folds. In a further process variant, the folds of a "concertina" fold have not the same length, but the ones in one direction are longer than in the other direction, such as indicated in FIG. 5D.

The present invention allows a beneficial combination of a cross-directional folding step with a stacking process, as it allows various exit spots, directions or orientations of the folded web materials. For example, after being folded, a web material (as may be seen in FIG. 4D) may exit the web path splitting means in a radial direction and enter a transportation conveyor (not shown) in the form of at least one helical screw feeder having its longitudinal axis parallel to a tangent to the drum. If the rotational speed and the pitch of that screw feeder are adjusted to the rotation of the drum, the folded web material may be gently transferred from the drum into the compartment of the screw, from where it may further be processed. This will then provide an easy way of stacking subsequent folded web materials, if the pitch of the conveyor screw is reduced, as also the height of the fins between two adjacent folded web materials may be reduced or the fins may end. At the end of this step, the folded web materials will be gently pressed against each other, and form a stack. Appropriate arrangement of web support means and receiving conveyor screw allow alternating orientation of the folded articles, e.g. if these are not folded symmetrically. To this end, a first folded web material may be directed to an exit on the left side of the third web support means, the next folded web material may exit on the opposite side thereof and enter a second flight of the screw feeder. Alternatively, this concept will allow splitting of the process stream by selectively directing certain web materials to one outlet and other to another. Thereby, the splitting can follow a freely programmable, yet preset pattern, or it can use on-line produced signals, such as quality inspection signals.

A further broad application area of the present invention relates to the "combining" a web material or a section thereof with itself, or with another section of itself, thereby exploiting the benefits of an easy to achieve cross-directional web-fold. Herein, the process element of "combining" comprises a first step of bringing at least two pieces, parts, sections, etc. into an adjacent positioning and to then perform an action for maintaining this relative positioning. Henceforth, a simple process example of a combining according to the present invention can be explained by considering the CD-folding process as described in the context of FIG. 4, with a further process step of applying an adhesive onto the trailing section of the web material, such as at the position of the tucker means 390. In a first combining step, the adhesive is combined with the web material, and in a second combining step, the sections of the web material are combined to each other. Similarly, as will be explained in more detail for application example A-3 herein below, both the front and the trailing section of a folded web material following the description for FIG. 3 may be glued or welded together at the longitudinal edges of the web material sections. Upon cutting a notch into the longitudinal edges of the centre section, thereby removing the glued or welded edges in this section, the combined web material would have a form of a pant, with two openings next to the cross-directional fold and a further opening at the opposite end of the web material. In a further modification, the notch cutting may take place before the web material reaches the web path splitting means.

As the present invention has a particular advantage of allowing close control over the positioning of the various pieces or sections even at high speed (i.e. overall web path speed), it allows novel combining operation such as slot/tab insertions as detailed herein below (Application example A-3).

The combining of various section of a web material can also be advantageously employed such as when sections are to be reinforced for withstanding mechanical stress, or for increasing "basis weight" depending properties (such as when laminates comprising absorbent material are folded for an increased absorbency per unit area and further wrapped to contain the absorbent material, such as further explained in application embodiment C-3). It can be employed to seal web materials being folded into a bag form (such as tea-bags), which may or may not be filled. The present invention provides also a very easy to use as well as versatile tool for the combining of a web material with another material. This other material can be in any form, such as when liquid materials are applied, three dimensional articles are wrapped. Particular benefits arise from the present invention, when the other material is also in the web, thread, or in a sheet form. For the present description, a web material as handled or treated as described hereinabove is considered a primary web material, which may be combined with a secondary web material, which may or may not be handled according the present invention before being combined with the primary web material. Thus, the primary web may be CD-folded as described hereinabove, and a secondary web material may just be laid over the primary one or the secondary may be CD-folded such as on a secondary drum. When two or more drums are used, their relative positioning may be arranged in any suitable way, such as having one common axis of rotation, or parallel axes, but offset such as in height, or their axes may form a right angle, optionally being offset.

The primary and the secondary web material may have the same orientation, e.g. if both travel on a parallel web path, and both are combined "lengthwise", i.e. the x-direction or machine direction of the primary web material is aligned with the x-direction or machine direction of the secondary web material. Thereby, various "laminated" structures may be produced, The present invention also shows particular advantages if a secondary material is combined with its secondary x-direction being perpendicular to the primary x-direction of the primary web material. A typical application would be the combining of an elastically extensible secondary material being stretched in its machine direction and being combined with a primary web material in cross-direction, such that the contracting forces of the secondary web material act in cross-machine direction of the primary web material, such as explained in more detail in application example A-6 herein below.

Generally, a secondary web material can be delivered in an essentially continuous form, and be combined as such with the primary web material being essentially continuous during the combining step, both materials can be pieces or parts thereof, the two materials can have but need not to have essentially the same dimensions, both materials may have the same orientation (i.e. MD and CD being aligned), both materials may travel along a parallel or a non-parallel web path. The combining can be made of sections of one material or can be made with two or more materials or parts or pieces thereof.

The combining can also be the complete or part of a packaging process, whereby the web material may serve as packing or wrapping material around another material such as an article to be packed, or may be the packed article.

The other material with which the web material is to be combined can be fed to the combining zone via many different ways, such as tangentially or radially to the outside of the drum, perpendicularly to the drum planes. It can also be fed into the centre part of the drum, from where it can move radially outwardly towards the web handling sections.

The decoupling of the web movement from the overall web path and the relating speed and the exact positioning of the combined parts allows the use of various other combining technologies, such as buttoning, sewing, or even forming knots.

APPLICATION EXAMPLES

The present invention as a basic process allows application in very many fields or technology sectors. The following specific application examples will support this, but should not be seen as limiting in any sense. Of course, the classification into application areas cannot be univocal, such that the packing of textile materials may evenly fall into the areas of textile handling as well as packaging.

A—Application Area: Hygiene Articles

In the manufacturing of hygiene articles, such as absorbent articles like baby diapers, feminine hygiene articles, or adult incontinence articles, many webs are used for various applications in large quantities and converted at very high production speeds. The present invention provides particular benefits in this context.

Disposable, absorbent articles typically include a thin, flexible, liquid-impermeable backsheet, an absorbent pad or panel on the backsheet, an overlying (i.e. oriented towards the wearer during use) liquid-permeable topsheet. Each of these components may be supplied in the form of a continuous web to an apparatus which forms, guides, combines, and secures the components together, often referred to as converter. Some types of disposable absorbent articles, such as diapers, typically include other components, such as elastic bands in the crotch area of the article to provide enhanced containment and leakage-resistance. Other features may include adhesive-coated tape tabs for securing the article to the wearer, a landing zone target tape against which the tape tabs can be securely, yet removably applied, or elastic waist elements to provide enhanced fit and comfort. While a variety of different mechanisms have been developed for combining the above-discussed components to form a complete article, it is preferable to employ such mechanisms along a processing line for controlled operation together to fabricate the article on a continuous basis as the major components move along the processing line. A typical manufacturing process for hygienic articles is described in EP-A-589859. A system for the in-line fabrication of disposable absorbent articles may comprise a series of modules, which may be joined in a linear array. During operation, individual mechanisms are performed continuously such as by means of electric motors to continuously operate on moving webs and other components of the article. In a preferred embodiment of the present invention, a web path splitting means may represent one such module.

Also known are processes employing drums for creating a cross-directional fold in such a manufacturing process, such as from EP-A-0974232 as discussed herein above. Whilst the general teachings of these publications are incorporated herein by reference, the following specific examples will clarify the functionality as well as the benefits of the present invention.

Example A-1

This example relates to the treatment of a web material in the manufacturing process, whereby the treatment requires a longer treatment time than is available in the main production "race track", i.e. the overall web path speed $v_0$ is too fast for this process step to be executed properly. Such a web material may be a fabric, such as a non-woven topsheet, or a plastic film backsheet, or the combination of these two elements with an absorbent core.

Typical treatment steps are the attachment of elements to the web material. Examples for such elements are plastic web pieces such as may be leakage prevention means (often referred to as waistshields), or plastic sheets enabling the closure of the finished article during use. Such sheets may be cut from a roll by a well known "cut-and-slip" unit, and may be applied to the web material in a "stamping" operation or by means of a transfer roll. Such web materials may be applied by using adhesives or by welding compatible materials (such as polypropylene non-wovens or films). Such application processes often require relative long processing times, such as more than 10 msec, which can not be readily achieved at overall web path speeds exceeding 10 m/sec on modern production lines.

Henceforth, a web path splitting means, such as in the form of a drum can be introduced into the web path as shown in principle in FIG. 2, thereby extending the treatment time. As shown in this example with six web handling sections, the treatment time will increase by a factor of six or more. The drum rotates, preferably at a constant speed. The tangential speed of the drum $|v_{Dr}|$ close to its periphery (i.e. where the web contacts the drum) is preferably the overall web speed $|v_0|$ (or "race track speed"). In order to allow flexible web material lengths being convertible on the drum, the design as schematically shown in FIG. 3 can be applied. The pitch (i.e. the web handling section length 501 in FIG. 3) can be adjusted to the smallest size and excess length of larger sizes is "folded underneath" the first web support means (330), optionally by means of a second (340) and/or a further support means (350). After the web treatment step is performed e.g. by web treatment means 400, the "folded excess length" can be pulled out to the full length of the web material for further processing.

The web support means may comprise web fixation means such as vacuum suction boxes, whereby the appropriate suction can be readily adjusted by a person skilled in the art for the web materials actually in use.

Example A-2

This example relates to the treatment of continuous webs or discrete parts thereof. The schematic diagrams of FIG. 3 may be used for explanation. The relative speeds and directions of the first (330), and/or second (340), and/or further web support means (350) are predetermined such that discrete pieces of the web material may be manipulated at an appropriate relative speed for a treatment equipment 400, which may be stationary relative to the frame of the support means (e.g. fix on the drum on which e.g. various vacuum belts as support means are mounted). Alternatively, the manipulating equipment may be relative stationary to the speed of the support means, thereby allowing operations which do not allow for any relative movement between the equipment and the web material. In this case, the treatment means 400 as shown in FIG. 3C could be arranged movably on a path parallel to the web support means surface, and move to the left, when the leading section 112 is pulled into the gap 380, and to the right, if the leading edge is released from the gap 380.

The treatment step in this example could be heat embossing or a welding process, wherein a heated anvil may be pressed against a composite web material for combining layers. In order to allow heat transfer to take place, a certain time is required, during which the anvil is preferably not moved relative to the web material.

Example A-3

A particular execution of example A-2 is to perform treatment operations on folded web materials, in particular when an exact registry of different folded parts (e.g. leading/trailing end) is required and/or parts of the web material are elasticised, i.e. have a tendency to contract (or be contracted by an elastication means). Such operations may include combining parts of the web material to each other, such as by gluing, or welding, or applying macro fasteners such as slot-and-tab systems.

A specific example is the butt seaming of lateral parts of the front end trailing part of the web material, thereby creating a closed structure such as can form the waist part of pant type article. FIG. 7 shows schematically a web handling section such as depicted 301, . . . of FIG. 2. A web material piece may be cut off a continuous web by means of an anvil/knife system 265, which may be affixed to the web handling section such that each web handling section comprises an anvil/knife system. Alternatively, either the knife or the anvil may be affixed to each web handling section, and the counterpart be affixed to the frame of the drum, such that it would be required only once for interacting with each of the counterparts of the web handling sections. As indicated in FIG. 7B, the piece of the web material is folded between support means 340 and 350, so as to position the first and the second section in juxtaposed positions to each other. The support means have a width (in the y-direction) less than the width of the web material, at least in leading and trailing section thereof (in the centre section, the web material width may be reduced by cutting in a separate process step). Bonding rolls 400 are arranged such they interact with the web material sections projecting outwardly from the web support means so as to bond the front and rear section to each other, thereby forming the desired closed structure, which may form the waist region of a pant type diaper. In this arrangement, the front and rear sections can be positioned in a very controlled manner, such that the sections are well registered, thus allowing a very neat bond. After the bonding, the web material may be extracted from the drum, such as by a web guide means 307 (the web guide means 307' belongs to the adjacent web handling section).

Figure 8C:
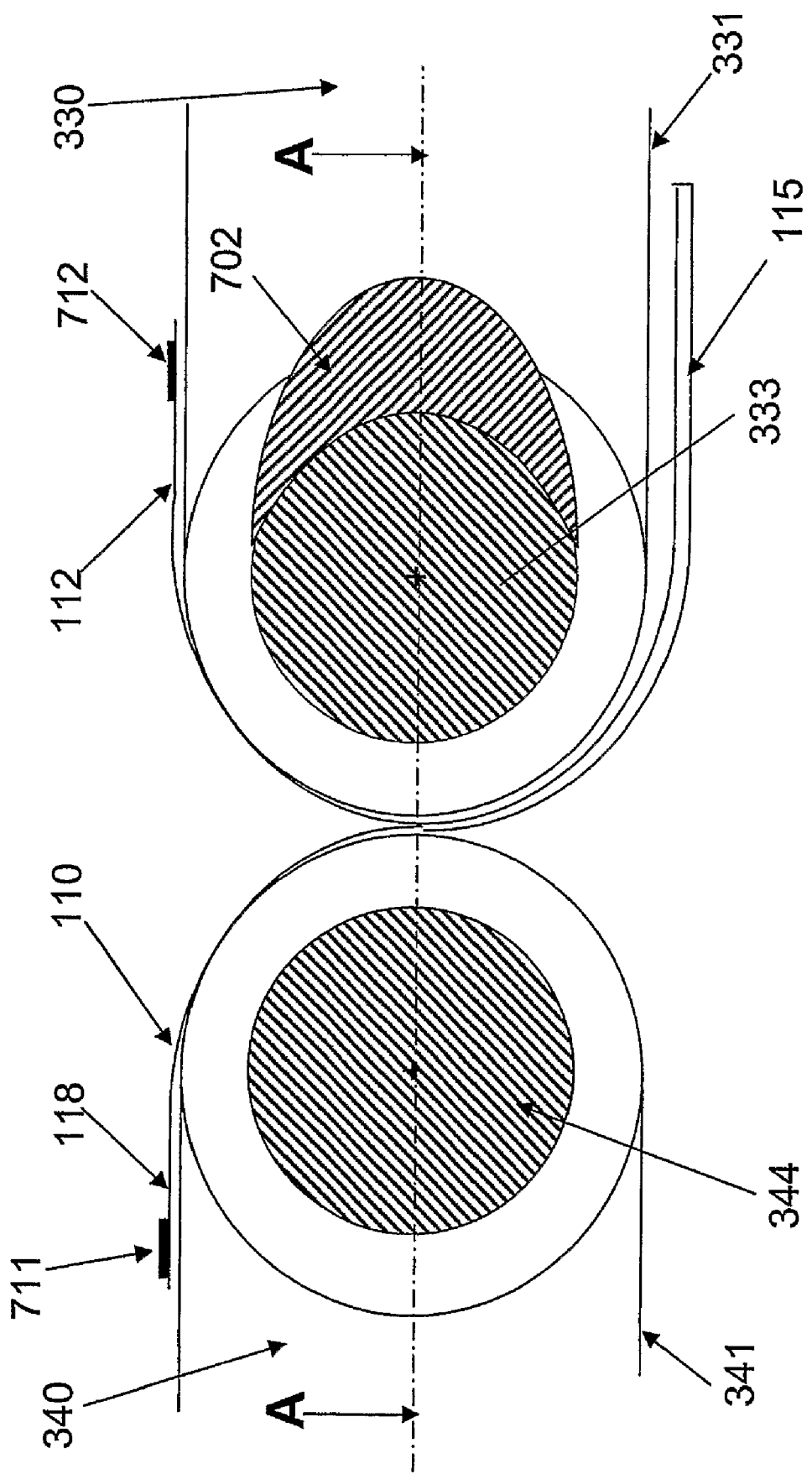

Instead of permanently bonding the front and rear sections to each other, these may be connected by applying a prefixed slot-and-tab fastener system, such as known from U.S. Pat. No. 6,669,618, which is for the general description of such systems incorporated herein by reference. Using the schematically drawn up FIG. 8, it is now explained how such process steps are executed by using the present invention. FIG. 8E schematically depicts a piece of a web material, which may be an almost finished absorbent article 110, with slots 711 already attached to the rear/trailing section 118 and tabs 712 already attached to the front/leading section 112. Starting from a continuous web, an article may already be cut such as by a cutting equipment 265 as indicated in FIGS. 8A and B, where a segment of a web handling section is representatively shown. The task is to fold the web piece such that trailing and leading sections are in a juxtaposed position, and to insert the tab 712 through the slot 711. This can conveniently be achieved by applying the folding technique as already explained, and again shown in FIG. 8B. FIG. 8C represents an enlarged view of the gap region 380 (excluding the web), in particular the belt drive support rolls 344 and 333 of the web support means 340 and 330, respectively, in the area where the tab and slot of the article are to be positioned, i.e. positioned laterally outwardly (left and right relative to the direction of movement). In this region, the support roll of the second web support means 344 is designed to have a circumferential groove 703, whilst the juxtapositioned support roll 333 of the first web support means is designed to have a cam in the form of tongue 702, see FIG. 8D, showing a cross-sectional view of details as indicated in FIG. 8C. The drive of the first and second web support means is programmed so as to phase the cam 702 with the tab element 710 when this part of the web is pulled through the gap 380, such that the cam pushes the tab through the slot element 711 overlaying the groove 703. Once the tab is inserted through the hole, the now folded and "pre-fastened" article may be further processed, such as being moved to a stacking equipment as explained hereinabove.

Example A-4

This example relates to cross-directional folding of web materials, as is shown in FIG. 4. The dimensions of the web material prior to folding may vary, and also the resulting dimensions of the folded web materials can be defined very freely without hardware changes. The folding may be a one-fold or a multiple fold. The folding direction ("inwardly"/outwardly") may be the same throughout the multiple folds or may vary. The folding in cross-direction may be combined with folding in longitudinal direction.

Thus, this provides a very flexible folding mechanism in the context of disposable absorbent articles, such as baby diapers, where tri-folding may be a desired feature. When being delivered to a web splitting means, such as a drum as described in FIG. 2, the almost finished articles still form a continuous composite web material, which may be essentially unfolded, or which may already be folded by conventional methods along a longitudinal fold line. Thus, for a typical baby diaper, the front and rear "ears" may be folded inwardly. When the web material arrives at the drum, it may be cut by an anvil/knife system (not shown in the figures) into individual pieces as described hereinabove, and may—by respective forward and rearward movement of web support means—be folded as depicted in FIG. 4. When the third web support means 350 moves at the first contact with the web material towards the right, the front/leading end of the diaper will be folded inwardly, forming an "e-fold" as indicated in FIG. 5B. Otherwise, a movement to the left would leave the end section open, forming a "z-fold", as shown in FIG. 5C.

Example A-5

After the folding and/or pre-combining step as described in examples A-3 or A-4, the discrete web materials may leave the drum system and may be picked up by a screw feeder apparatus having its longitudinal axis parallel to a tangent to a drum, as described in the general part section. With varying pitch of the screw feeder over its length, and decreasing height of the screw fins, subsequent articles will be moved closer and closer to each other, until a stack is formed, which then may be removed, such as towards a packing station. This will provide a very gentle means for removing articles from a production, providing a distinctive benefit over conventional stacker system, wherein often the folded articles "shoot" with the overall web path speed $v_0$ into a stacker compartment, where they are abruptly stopped, often resulting in deformation or even mechanical damage.

Example A-6

This exemplification relates to the combining of a primary web material with a secondary web material, whereby the latter may have a web path essentially parallel to the path of the primary web material, or a non-parallel path. The combined material may have different dimensions and/or different degrees of extensibility/elasticity (stretch). Thereby, the secondary web materials may be combined with the primary web materials in a "cross-directional" positioning, i.e. the (original) length direction of the secondary web material may extend along the cross-direction of the primary web material. Optionally, the secondary web material may be elastic, and may be extended while being combined with the first web material, thereby imparting cross-directional contraction to the primary web material.

Herein, a first drum is designed analogous to the ones described herein above, and depicted in FIG. 2, except that only a first and a second web support means are required. A second drum is arranged with a centre of rotation being straight aligned with the centre of rotation for the first drum, and both may be jointly driven on one axis. The second drum may have similar dimensions and design as the first one, in particular the same segmentation, such that each segment on one drum has a corresponding segment on the other.

Such a set up is exemplarily depicted in FIG. 9A, showing in the upper part schematically the drum segment of a first drum 810 with a first web support means 1330 and the second web support means 1340. A web material 1100, which may be a continuous web or a sequence of discrete web pieces, extends in FIG. 9A essentially straight over both web support means, i.e. over the initial contact regions. In FIGS. 9B and 9C the web material is pulled into the gap 1380, which may be achieved by reversing the direction of move of the first web support means 1330. In FIG. 9D, the web material is pulled straight again, such as by accelerating first web support means 1330 in the original direction (in the figure to the right hand side).

Whilst the second drum 820 is located behind the first one, FIGS. 9A-D show the elements of the two drums not in their true geometrical relation. Thus the segment 2300 of second drum 820 is depicted under the segment 1300 of the first drum 810, although it is located behind it.

A web treatment section of the second drum 820 requires only one web support means 2330; however, this allows a change in direction of the web path, in this example of 90°. To achieve this, the continuous belt 2331 runs over at least three support rolls, at least one thereof (2333) being programmably driven as well as at least two free support rolls 2334, as shown in the lower section of FIG. 9A. Accordingly, the second web 2100 comes from the left, and is—after it may have been cut by web cutting unit 2265 into pieces 2110—turned at a right angle downwardly by following the change of direction on the web support means 2330. FIG. 9B depicts this web material piece 2110 cut to its x-direction length (or machine direction of the secondary web material) already moved into such a position. FIG. 9H illustrates the general principle in a perspective view by showing regions or sections of the webs at different stages of the process as these travel through such a process set up.

At that point in time, the web support means 2330 is rotated around an axis as indicated by connecting hinge points 2339. This axis is parallel to the web path direction of the primary web on the first drum, such that the web support means 2330 rotates into the first drum and fits therein. In FIG. 9C, this is indicated by now showing the top side of the web support means 2330 after rotation, i.e. now showing the drive and free support rolls of the web support means in a top view rather than in the cross-sectional or side view as in FIGS. 9A and B. Also web material piece 2110 is shown in this view, here indicated by having a different dimension than in FIG. 9B, namely the original width dimension, here indicated to be smaller than the original cut length in FIG. 9B (see also FIG. 9H).

Figure 9E:
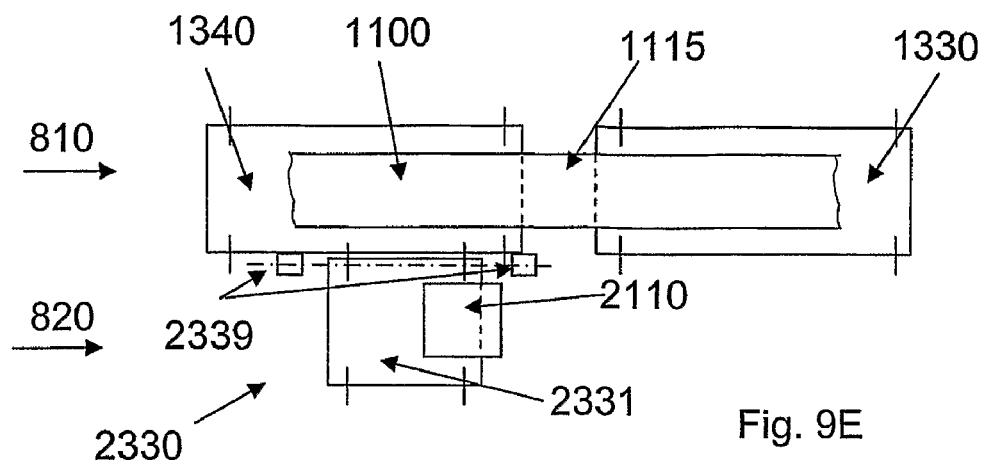
Figure 9F:
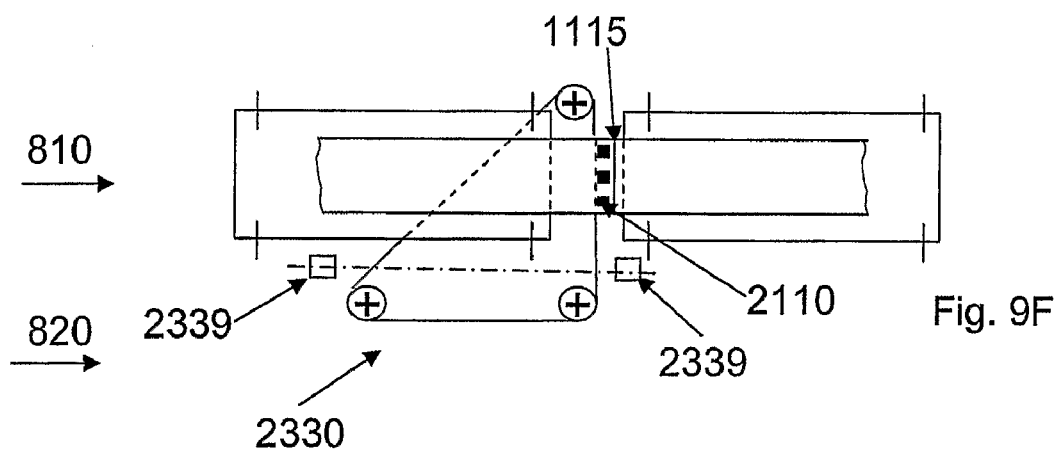
Figure 9G:
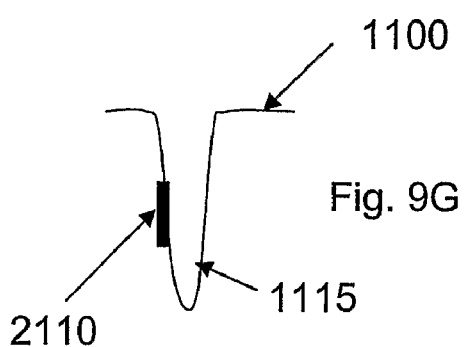
Figure 9H:
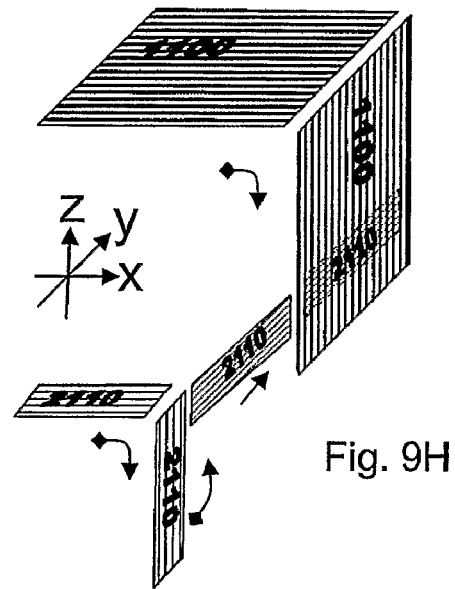

This rotation is further illustrated with FIGS. 9E and F, showing a simplified top view corresponding to FIGS. 9B and C respectively. In FIG. 9F, the folded region 1115 of the first web cannot be seen, and the cut piece 2110 is shown still held on web support means 2330 of the second drum, now shown to engage into the first drum. Thus the cut piece 2110 and the folded regions of the web 1115 are in a juxtaposed position, and a combining means 1400 (as indicated in FIG. 9C only) may then transfer the web piece 2110 to the folded region of the web 1115 of the primary web, such as by gluing or welding. FIG. 9G illustrates the combined but still folded composite.

FIG. 9D shows the situation after the web on the first drum 810 has been pulled straight again, and the web support means 2300 has been rotated back to its initial position in the second drum, ready to receive the next material. As can be seen in FIG. 9H, piece 2110 is now oriented such that its original machine direction (i.e. the direction of the web material 2100 as it was supplied such as from a roll) is now across the web material 1100. This can be of particular benefit, if the secondary web material has elastic properties. Then this can be fed into the process in a stretched or elongated state, which can be maintained throughout all process steps. By that, this will impart cross-directional elastication to the web 1100.

Example A-7

A further specific application of example A-4 (folding of web materials) applies to absorbent cores, which may be in the form of absorbent web materials, which may comprise particulate absorbent materials, sandwiched between continuous support layers, such as tissues or non-woven materials.

When a specific length of such a composite is cut for being inserted into absorbent articles, a typical problem relates to the loss of particles at the cut edge. A solution to this problem uses the folding principle so as to tuck the cut ends inwardly, as depicted in FIG. 10 for the rear edge region 119. To this end, the continuous web is fed into the initial contact regions of a first and a second web support means as indicated in FIG. 10A, and cut to the appropriate length by separation means 265. Thereafter, both web support means change their direction of movement, and the web is pulled into gap 387 between the second web support means 340 and a web guide means 307, such as by being held by vacuum in the region of the roll 344 of the second web support means.

In a consecutive process step illustrated also in FIG. 10, zones of varying absorbency may be created. For ease of manufacturing, it may be preferable, that the absorbent web materials have a constant absorbency per unit area, such as may be accomplished by distributing the absorbent materials at an even basis weight. From a functionality perspective for the absorbent article, however, it may be desirable to have regions with higher absorbency than others. This can be achieved by appropriately folding the absorbent web material, as depicted for the front region 112 in FIG. 10. After the rear end region 119 has been tucked in, the movement direction of the second web support means 340 is reverted, whilst the one of the first web support means 330 is maintained with the front section 112 of the web thereon. Thus, a central region of the absorbent web 115 will be pulled into the gap region 380, thereby doubling the layers and hence the absorbency in these regions. Once the front section is fully pulled into the gap, a web piece as shown in FIG. 10E is formed.

B—Application Area: Textile Handling

Garment manufacturing is an increasingly competitive industry wherein numerous innovations have been made in an effort to reduce the labour and time expenditure per garment. In order to improve productivity, many aspects of garment production have been automated. For example, it is common practice to use automated sewing machines to stitch a seam along one side of a garment. In doing so, the appropriate garment portions are placed on a conveyor which carries the portions through the sewing head where the actual sewing takes place. The proper placement and alignment of the garment portions on the conveyor is a major requirement for successful operation of such automated machinery.

Often, textile pieces, which are to be combined to form a garment are placed on a stack, and as such would not be considered "web materials" in the context of the present description. If, however, the pieces of a stack are positioned e.g. on a belt system to then form an essentially continuous sequence of pieces, this would then be considered as web materials in the present context.

Example B-1

As laid out in the above exemplifications, production of simple disposable articles, such as disposable underwear or surgical gowns as may be produced from non-woven material as described in U.S. Pat. No. 6,062,444, may be advantageously carried out by employing the present invention, following the application examples for the hygienic articles, such as for side seaming or cross-directional elastication.

However, even more benefits arise for more complex articles. In order to arrive at neat borders or selvages, various parts of one or more textile materials need to be brought into appropriate positioning as described hereinabove, and automatic sewing machines, such as described in U.S. Pat. No. 5,174,480, are used as combining means.

The teaching of the present invention can also be readily re-applied to a multi-station system, as described in WO-A1-90/03739, wherein the flexible work pieces are transferred via an interchange area from one work station to another by a transfer means, such as a robotic arm. Following the present teaching, the separate workstations can be realized by subsequent process steps in one web handling section.

The process steps to work on textile web materials may be achieved by equipment, which is stationary to the overall machine frame (and thus one equipment may apply the treatment for the subsequent web handling sections such as of a drum). It may also be stationary on the web handling section, or it may be moveable on a frame, which is affixed to the web handling section, such that, for example it travels along the web support means relatively fixed to the web material.

The controlled web support system of the present invention is also particularly suitable for handling lightweight and porous materials, such as lace, without the need for creating a particular mask (such as described in WO-04/060092-A1). In analogy to example A-6, it allows readily for the application of elastic elements to textile articles. It also allows for application of heat treatment steps, which may render a textile material and the resulting garment elastic (such as when following the teaching of US-A1-2003/041425).

Yet another problem in the textile industry applies to turning web materials such that the desired side of the material is facing "upwards" respectively towards the appropriate facing side of another material. Thus, a side detector means, such as optical devices as described in EP-A1-0374314, may provide a signal upon which such a web piece materials is directly transferred from a first to a second web support means, if positioned "right side up". In case it should be turned upside down, the web piece would be pulled into the gap between the two web support means (such as by remaining fixed on the surface of the first web support means). Once the trailing edge reaches the gap region, this is transferred to the second web support means, the first one reverts its direction of movement, and the web piece is pulled out of the gap onto the second web support means, now in a "right side up" position.

Example B-2

A particular problem as can be resolved by the present invention relates to inverting tubular textiles. Many textile articles comprise elements in essentially tubular form, such as trouser legs, sleeves for shirts, stockings, etc.; require inverting, such as being addressed in U.S. Pat. No. 5,392,970, relating to hosiery items, or in U.S. Pat. No. 5,628,435, relating to inverting shirt sleeves after sewing.

The present invention provides a simple solution to such a problem, by combining the forming of the tubular element with the inverting step. The overall set up of the web support means looks similar to the ones arranged in FIG. 1 or 3, except, that the third web support means 350 is positioned (with directions and orientations as shown in these figures) above the first web support means 330, and a web gripper means 398 would be positioned at the tip of a mandrel extending above the web support means in a "downstream" orientation into the gap region 380—see FIG. 11A. The web gripper means may be a vacuum suction tip, connected to a vacuum suction 410.

The tubular materials are formed from flat web materials 110, such as may be provided as pre-cut pieces or as an essentially continuous web. In the presently considered set-up, the web materials are picked up by the second web support means 340 first, and then moved downstream to a first web support means 330. The edges extending in longitudinal extension both of the web material and—for the present description—of the second web support means 340, to which these web materials are fed with preformed sides edges, or on which the side edges may be appropriately cut. Whilst being transported on the second web support means 340, the side edges are folded upwardly, such as by guide means (not shown), until the opposite edges come into contact, such that the tubular element may be formed by combining these edges, such as by sewing, gluing, welding or any other suitable combining mechanism by combining means 400. The tubular structure can be cylindrical, if the side sections a parallel, or can be of another shape, such as a conical shape, when the side edges are tapering.

The web gripper means 398 extends from the zone before the combining apparatus through the then formed tubular structure to the gap region 380. When the thusly formed tubular material is further moved by the second web support means 340 towards the gap region 380, the gripper means will fix the leading edge thereof, such as by vacuum suction. With continuing web material transfer from the second web support means 340, the material will bulge upwardly, and will be affixed, such as by vacuum suction, and optionally supported by tucker means 390, to the first and third web support means 330 and 350. Optionally, the tip of the mandrel can be reciprocating between the combining means and the first and third web support means, thusly transporting the combined tubular element closer to these web support means so as to ease the fixation thereto. At the point as shown in FIG. 11C, the first and third web support means move at half the speed of the first web support means. As the fixation is at such a level, that the leading edge is released upon the backholding force of the web being held by the web gripper means 398, the tubular element will be inverted, as shown ion FIG. 11D, and may be further processed upon releasing the holding, such as the vacuum 410.

The first and the third web support means are moving the web material away from the gripper point at the tip of the gripper means, i.e. in the exemplifying figure to the right hand side. If the original web material is an essentially continuous material, it may be cut to the appropriate length on or before the first web support means. Once the web material piece is completely inverted, the gripper means will release the affixed end and the inverted tubular web material may be further processed.

Example B-3

The problem of folding textiles such as for preparation of or during the packaging step has been described such as in US-A-2001/050295 in the context of shirts, US-A-2003/052141 in the context of linen. In U.S. Pat. No. 6,062,444 a particular problem is addressed, relating to surgical gowns, which not only require a very particular kind of folding to allow easy donning under sterile conditions, but also require sterile conditions for the preparation including the folding of the article. The present invention provides simple and versatile solutions to such problems, and the skilled person will—upon introduction to the concept as described herein—readily arrange the web supporting means and their respective required programmed movements not only to such problems, but also to similar ones, such as posed together with a relatively complex solution in the context of forming and folding round cut edges as described in WO-00/035306A1, or in U.S. Pat. No. 5,996,861, wherein the handled material, a delicate hosiery material, requires particular and rather complex conventional equipment and process set up.

The present invention also allows for the folding of web material pieces to be performed while including an article support member, such as a cardboard piece as typically used in the packaging if shirts, which may be introduced into the process from a stack, or also as a web material, such as from a roll. In the latter option, the stiffness of the article support means may be increased, if two thinner materials are combined to form a laminate of the desired stiffness. The present invention may further be applied to the formation of stacks of textile articles, in analogy to what has been described in the context of the hygiene articles.

Example B-4

A frequent problem posed in the textile industry relates to the application of closure elements, which are preferably not only for repeated closure and opening, but also delivered to the end-user in a combined or "closed" state. Typical examples are related to buttons, eyelets, and the like, for which the application Example A-3 as described for hygienic articles may be readily re-applied. Also the application of slide-fastener, such as described in U.S. Pat. No. 5,138,763 or EP-A2-00292110 in general terms, may use a particular advantage of the present invention, namely the exact registry positioning when combining respective materials.

Example B-5

Yet another application area relates to a hitherto very poorly developed technology, namely the bow forming or knot tying, such as may be advantageously applied when forming decorative bows, such as further laid out in WO-A1-99/62363, or when combining an essentially endless material, such as a line, to an object, with typical applications being explained in U.S. Pat. No. 6,834,894 relating to fishing equipment, or in US-A1-2004/0222634, relating to threads being attached to tea bags, where the use of metal stapling is often undesired. To this aspect, the present invention provides a very accurate positioning, such that entangling or knot forming aids may be readily inserted through as described for the slot and tab fastening of application example A-3.

C —Application Area Packaging

In the area of packaging, the present invention can provide a multitude of solutions, among other reasons because the reciprocating movement of a web support means under very controlled conditions allows coverage of the "upper" and "lower" surface, and the potential for adding further process steps, such as rotational movements, or combining steps, such as gluing or welding.

Example C-1

As developed already hereinabove, the present invention allows ready use and converting of delicate, supple, or flimsy materials, either as the packaging material, but also as the goods to be packaged. After delicate materials are prepared for packaging such as by being folded as described hereinabove, these may be stacked, hitherto such as by a relative complex method as described in EP-A-00894725. By using the principles as laid out for the application examples in the hygiene area, a skilled person will readily arrange the web support means so as to match the particular stacking and wrapping requirements.

In particular, in the context of elastic or elasticated material, such as laminates comprising elastic material as described in WO-A1-00/044627, the present invention allows direct combination of the forming of the laminates with the packaging at a very simple design set up to produce a laminate under extended or stretched conditions, but relax this material prior to packaging, further providing alternatives to the so called "festooning" process as described in US-A1-2002/046549.

Yet another exemplary application relates to the packing of relatively compressible material, such as described in U.S. Pat. No. 5,459,979 or EP-A1-00420071, both relating to the packing and folding of cellulose or paper napkins. Hereby, the benefits of the present invention allow the direct combination of the folding steps—and in particular cross-directional folding—with the stacking and wrapping. The controlled conditions also favour the application under hygienic conditions, such as may be particularly relevant for food packaging, such as described in EP-A1-00482334, or as described in U.S. Pat. No. 654,669 relating to mechanically demanding design for packaging fragile foodstuff.

For such cases, the present invention allows not only for the exact positioning of the packaged good and the packaging material relative to each other independent of pressures exerted on the packaged good by having the packaging material being guided by the various web support means, but by appropriately spacing the web support means from each other, it even allows essentially compression free guiding of the packaged good.

Example C-2

The multi-purpose functionality of the present invention can be further exemplified when considering packaging of individual pieces or groups of such pieces into an essentially continuous wrapping web material. The problems as raised in US-A1-2002/189201 related to the packing of pieces of food, optionally including an inspection and/or sorting step, such as by automatic weight control, is readily resolved by the present invention, such as by feeding the pieces either tangentially to a first web support means carrying the packaging material in the web form, or inserting the pieces in a direction parallel to the axis of a drum as a web splitting means. A common problem for packaging is the combination of several items in a group, such as described in EP-A1-00825113 relating to multilayering of cigarettes, or in U.S. Pat. No. 5,699,651, relating to combining a continuous line of goods such as bottles or cans to bundles such as a "six-pack". To this end, the present invention allows readily identifiable solutions by the use of the predetermined programming of the movement speed and/or direction of the web support means as well as their flexible arrangement. Even the forming of appropriate packing materials from web materials may be accomplished by using the present invention, such as by combining the web support means with a forming device, such as a deep drawing device, so as to position the pieces into the thusly formed cavities.

Example C-3

Yet another particular application area for the present invention relates to combined forming of closable packing material with simultaneous filling thereof. Typical solutions to such a problem have been presented in WO-A1-04/054880 or U.S. Pat. No. 5,951,452 relating to tea or infusion bag forming and filling. According to the present invention, a continuous web of tea bag material may be guided between a first and a second web support means so as to form a loop in a gap there between, which may be side sealed by conventional sealing means, such a hot sealing. The tea or infusion material may be supplied by any conventional means in a metered continuous stream or in individualized small heaps or piles such as via an additional support means, and may be supplied radially to the drum, or tangentially, pneumatically, or by gravity. Once the material is put into the side sealed pouches, the web material may be cut and completely closed, such as by sealing. In a particular embodiment this bag forming may be combined with attaching a thread thereto, such as by tying a knot as described hereinabove. Instead of the granular material of teas or infusions, semi-solid or even liquid materials may be supplied into a pouch of web material. Optionally, the material may thereon solidify, such as in the case of candy wrapping, or which may remain essentially liquid, such as may be for single serving packs, such as for food additives, such as mustard, oil and the like, or for personal cleansing, such as shampoo or soap.

Example C-4

Further application areas in the field of packaging will be readily apparent to a skilled person, such as, without intending any limitation by the exemplification, packing article or goods of variable length into essentially continuous webs. The packing of itemized articles may be combined with in-situ forming of air-cushioning materials, such as be creating air-filled pouches in parallel to packing the article, and inserting all into suitable packs such as boxes or cartons.

D—Application Area Printing/Bookbinding

A further field of particularly suitable application for the present invention relates to the handling of printing products, such as bookbinding, enveloping, sleeving or the like. It will be readily apparent, that the web splitting means allows treatment times for the individual steps, which can be much longer than in the main "race track", and the various web support means providing flexible combination of speeds and direction allow virtually any desired combining or positioning of materials. Even the printing itself may be done whilst the respective web material such as the printing paper are mechanically processed, such as by being sized to the appropriate dimensions, or oriented, or so on. The thusly treated and prepared printed web material pieces may be directly fed into the packing step, such as may be other printed envelops, or plastic film wraps or the like. Similarly, stacks of appropriately sorted printed matter may be combined to form complete books, such as by gluing or stitching and/or combining with spine inserts. In this case, a series of stacks made from web materials can also be considered as an essentially continuous sequence of web material pieces.

E—Other Areas

The above exemplification should not be considered limiting in any way, but will teach the skilled person how to approach applications in even other areas and fields.

The invention claimed is:

1. A method for handling a web material which is an essentially continuous web or an essentially continuous sequence of pieces of an essentially continuous web, on a web handling equipment having an overall web path connecting a web supply means with a process section end point, said web material comprising at least a first and second section being connected and spaced apart with the first section being oriented along said overall web path more towards said process section end point than the second section, characterized in that said method comprises the steps of:
   a) providing said web material on said web supply means;
   b) moving said web material from said web supply means towards said process end section along said overall web path at an overall web path speed |v0| relative to the frame of said web handling equipment;
   c) providing a web path splitter positioned along said overall web path and comprising at least a first and a second web handling section, each of these web handling sections comprising a section frame, and at least one web support connected to said section frame and comprising a freely programmable drive, having a surface which is movable relative to said section frame;
   d) splitting said web path on said web path splitter into at least a first and a second web sub-path, each running through one of said web handling sections; and transferring said web material along said web sub-paths to said web handling sections;
   e) handling said web material in each of said web handling sections by:
      1) affixing at least said first section of said web material to the surface of a web support in the initial contact region of said web support, without affixing said second section of said web material to said web support surface;
      2) changing the speed of said surfaces of said web support, while having at least said first section of said web material remaining affixed thereto, thereby changing the relative speed of said first section of said web material to a second section of said web material;
   f) thereby transferring at least parts of said web material out of the initial contact regions of said web support into an operating region of said web support or of a further web support, thereby forming a cross-directional fold in said web material;
   g) optionally performing further web handling or treatment steps on said web material;
   h) removing said web material from said web handling section; and
   i) providing said web handling section for repeated executions of the web handling steps d) to h).

2. The method for handling a web material according to claim 1 further comprising a web treatment step.

3. The method for handling a web material according to claim 2, wherein said web treatment step is a combining step, for the combining of a section or region of said web with another section or region of said web or with another material.

4. The method for handling a web material according to claim 3, wherein said combining is essentially permanent, preferably by gluing or welding of the web material.

5. The method for handling a web material according to claim 3, wherein said combining is a releasable combining, preferably of the slot and tab or button type.

6. The method for handling a web material according to claim 3, wherein said web combining step comprises the combining of said web material with a secondary web material.

7. The method for handling a web material according to claim 1, wherein said web path splitter is a rotatably mounted drum.

8. The method for handling a web material according to claim 1, wherein said web support comprises an endless belt surface.

9. The method for handling a web material according to claim 1, wherein said web support is a belt system, comprising an essentially endless belt, comprising a freely programmable electrical drive integrated into a belt support roll.

10. The method for handling a web material according to claim 1, wherein said web support comprises vacuum suction means for temporarily affixing said web material to said web support.

11. The method for handling a web material according to claim 1, wherein said web support is moveably connected to said section frame of said web path splitter.

12. The method for handling a web material according to claim 1 further comprising the step of receiving web material pieces and positioning said web material pieces in stack.

13. The method for handling a web material according to claim 1, wherein said freely programmable drive is an electrical drive.

14. The method for handling a web material according to claim 13, wherein said electrical drive is a servo motor.

* * * * *